US009492186B2

(12) United States Patent
Ghijselings

(10) Patent No.: US 9,492,186 B2
(45) Date of Patent: Nov. 15, 2016

(54) DEVICE AND METHOD FOR INSTALLING FEMORAL PROSTHETIC KNEE JOINT

(71) Applicant: Ignace Ghijselings, Ursel (BE)

(72) Inventor: Ignace Ghijselings, Ursel (BE)

(*) Notice: Subject to any disclaimer, the term of this patent is extended or adjusted under 35 U.S.C. 154(b) by 85 days.

(21) Appl. No.: 14/509,724

(22) Filed: Oct. 8, 2014

(65) Prior Publication Data

US 2015/0025537 A1    Jan. 22, 2015

Related U.S. Application Data

(62) Division of application No. 12/443,879, filed as application No. PCT/EP2006/009811 on Oct. 11, 2006.

(51) Int. Cl.
| | | |
|---|---|---|
| *A61B 17/15* | (2006.01) | |
| *A61B 17/17* | (2006.01) | |
| *A61B 17/02* | (2006.01) | |
| *A61F 2/46* | (2006.01) | |
| *A61B 17/00* | (2006.01) | |
| *A61F 2/38* | (2006.01) | |

(52) U.S. Cl.
CPC ......... *A61B 17/1764* (2013.01); *A61B 17/025* (2013.01); *A61B 17/155* (2013.01); *A61B 17/1725* (2013.01); *A61F 2/461* (2013.01); *A61B 2017/00407* (2013.01); *A61B 2017/0268* (2013.01); *A61F 2/38* (2013.01)

(58) Field of Classification Search
CPC ................... A61B 17/1764; A61B 2017/0268
See application file for complete search history.

(56) References Cited

U.S. PATENT DOCUMENTS

| | | | |
|---|---|---|---|
| 1,411,720 A | 4/1922 | Goodie | |
| 2,286,982 A | 6/1942 | Todd | |
| 3,025,853 A | 3/1962 | Mason | |
| 3,270,477 A | 9/1966 | Johnston | |
| 3,316,338 A | 4/1967 | Helmut | |
| 3,655,227 A | 4/1972 | Orloff | |
| 3,709,219 A | 1/1973 | Halloran | |
| 4,187,841 A | 2/1980 | Knutson | |
| 4,220,146 A | 9/1980 | Cloutier | |
| 4,501,266 A | 2/1985 | McDaniel | |
| 4,524,766 A * | 6/1985 | Petersen | A61B 17/154 606/184 |
| 4,566,448 A | 1/1986 | Rohr, Jr. | |
| 4,968,316 A | 11/1990 | Hergenroeder | |

(Continued)

FOREIGN PATENT DOCUMENTS

| | | |
|---|---|---|
| EP | 0 194 014 | 9/1986 |
| EP | 0 809 969 | 12/1997 |

(Continued)

OTHER PUBLICATIONS

International Search Report dated May 25, 2007.

(Continued)

*Primary Examiner* — Zade Coley
(74) *Attorney, Agent, or Firm* — Knobbe Martens Olson & Bear LLP

(57) ABSTRACT

Devices and method for performing replacement prosthetic knee surgery are disclosed in which a spacing means is introduced between the femur (1) and tibia (2) while the patella (9) is in place. The spacing means separates the femur (1) from the tibia (2) by an amount essentially equal to or greater than the required flexion gap (4). An alignment device (26) is used for performing femoral bone cuts, which device attaches temporarily to a fitted tibial plate.

33 Claims, 16 Drawing Sheets

(56) References Cited

U.S. PATENT DOCUMENTS

| | | | |
|---|---|---|---|
| 5,080,545 A | 1/1992 | McKinlay | |
| 5,195,854 A | 3/1993 | Nagayama | |
| 5,374,270 A | 12/1994 | McGuire et al. | |
| 5,425,490 A | 6/1995 | Goble et al. | |
| 5,540,696 A | 7/1996 | Booth et al. | |
| 5,597,379 A * | 1/1997 | Haines | A61B 17/1764 606/80 |
| 5,669,914 A | 9/1997 | Eckhoff | |
| 5,722,976 A | 3/1998 | Brown | |
| 5,743,691 A | 4/1998 | Donovan | |
| 5,769,850 A | 6/1998 | Chin | |
| 5,860,980 A * | 1/1999 | Axelson, Jr. | A61B 17/155 606/88 |
| 5,968,047 A | 10/1999 | Reed | |
| 6,287,308 B1 | 9/2001 | Betz et al. | |
| 6,520,967 B1 | 2/2003 | Cauthen | |
| 6,974,481 B1 | 12/2005 | Carson | |
| 7,273,500 B2 | 9/2007 | Williamson | |
| 8,343,190 B1 | 1/2013 | Mueller et al. | |
| 2002/0035368 A1 | 3/2002 | Schumacher | |
| 2002/0133164 A1 | 9/2002 | Williamson | |
| 2002/0156480 A1 * | 10/2002 | Overes | A61B 17/025 606/90 |
| 2003/0023312 A1 | 1/2003 | Thalgott | |
| 2003/0028196 A1 * | 2/2003 | Bonutti | A61B 17/025 606/87 |
| 2003/0040746 A1 | 2/2003 | Mitchell et al. | |
| 2003/0088252 A1 | 5/2003 | Kaikkonen et al. | |
| 2004/0122441 A1 * | 6/2004 | Muratsu | A61B 17/0206 606/102 |
| 2005/0085920 A1 | 4/2005 | Williamson | |
| 2005/0187560 A1 | 8/2005 | Dietzel et al. | |
| 2005/0256527 A1 | 11/2005 | Delfosse et al. | |
| 2005/0267485 A1 * | 12/2005 | Cordes | A61B 17/02 606/88 |
| 2006/0036257 A1 * | 2/2006 | Steffensmeier | A61B 17/1764 606/90 |
| 2006/0058785 A1 | 3/2006 | Fuchs et al. | |
| 2006/0089653 A1 | 4/2006 | Auger et al. | |
| 2009/0326544 A1 | 12/2009 | Chessar et al. | |
| 2011/0066186 A1 | 3/2011 | Boyer et al. | |

FOREIGN PATENT DOCUMENTS

| | | | |
|---|---|---|---|
| FR | 2 742 037 | 6/1997 | |
| FR | 2 857 576 | 1/2005 | |
| FR | WO 2005006993 A2 * | 1/2005 | A61B 17/025 |
| WO | WO 99/25263 | 5/1999 | |
| WO | WO 0202021 | 1/2002 | |
| WO | WO 03079912 | 10/2003 | |
| WO | WO 2005092205 | 10/2005 | |

OTHER PUBLICATIONS

Extended European Search Report dated Sep. 10, 2013 in patent application No. 12177282.6.

* cited by examiner

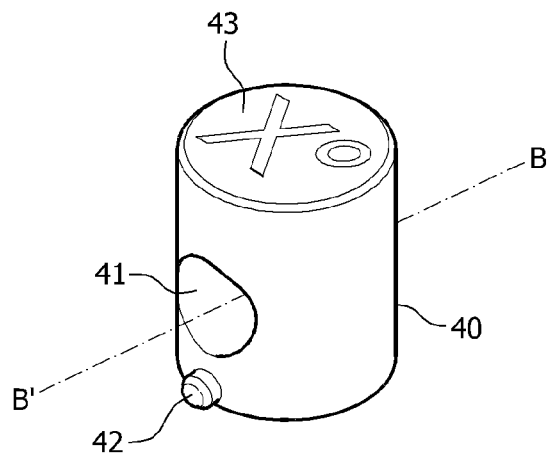
FIG. 13A
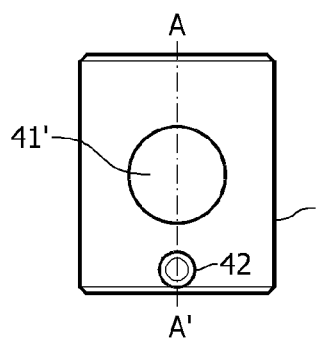 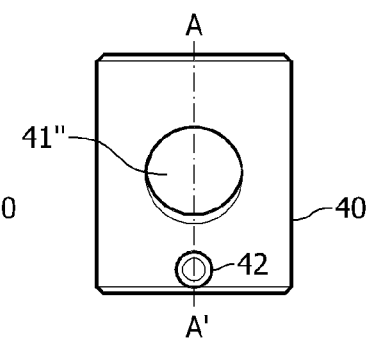 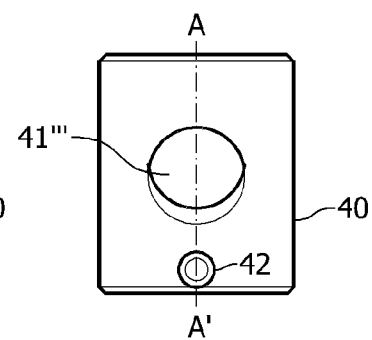
FIG. 13B    FIG. 13C    FIG. 13D

DEVICE AND METHOD FOR INSTALLING FEMORAL PROSTHETIC KNEE JOINT

CROSS-REFERENCE TO RELATED APPLICATIONS

This application is a divisional of and claims priority to U.S. patent application Ser. No. 12/443,879, filed Apr. 1, 2009, which is the U.S. National Phase under 35 U.S.C. §371 of International Application PCT/EP2006/009811, filed Oct. 11, 2006.

During surgery for fitting a prosthetic knee joint, a number of bone cuts are made to allow placement and orientation of the femoral component of the prosthesis, and to determine and form the joint gaps in extension and flexion 4 (see FIG. 1). The size and shape of these two gaps affect final orientation of the prosthesis, as well as joint tensioning and clearances.

Generally, the bone cuts are formed so that in extension the joint gap is perpendicular to the mechanical axis of the femur, while in flexion the joint gap is such as to place the femoral component in either neutral or external rotation and assure proper patellar tracking with the femoral component. To fit the femoral component the gaps created by the bone resections in both flexion and extension should be of dimensions to achieve the previous tension in between femur and tibia in flexion after the prosthesis is fitted. Therefore, the cuts must account for the thickness of the femoral and tibial prostheses, and so placed to maintain tension in the joint, and so align properly the prosthesis. There is difficulty in the art with achieving the correct alignment of femoral cuts because cutting the bones requires effectively dismantling the joint so the knowledge of the previous tensions and orientation is lost. When the cuts are incorrect, improper kinematics will arise as the joint rotates in use, and accelerated wear patterns or possible joint dislocation may occur.

After the prosthesis has been fitted, it may be necessary to perform soft tissue balancing. After balancing the ligaments should have the same tension in extension and flexion. The technique of soft tissue balancing has to be mastered carefully. In balancing the soft tissue, the surgeon will make cuts to the ligaments and muscles. Inadequate soft tissue balancing will lead to instability, pain and eventual failure. The soft tissue balancing has to be assessed several times so that the appropriate flexion and extension gap is achieved. Even when soft tissue balancing has been optimised by the surgeon, the subject must still undergo physiotherapy to regain a muscular tension corresponding to the best possible joint movement.

There is a need in the art for a method and technique for fitting the femoral component of a knee prosthesis which provides accurate bone cuts giving a same height of the extension and flexion gap, and that reduces or avoids the need for soft tissue balancing.

BRIEF DESCRIPTION OF THE FIGURES

FIG. 13A shows a three dimensional view sliding bushing of the present invention.

FIGS. 13B to D show a front elevation of the bushing of FIG. 13A, each view depicting a hole having a central axis at different angles.

SUMMARY OF THE INVENTION

Figure 1:
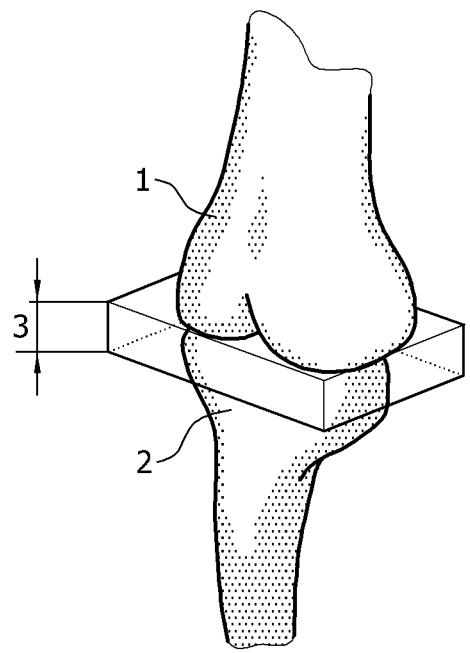
FIG. 1 shows a three dimensional view of the femur and tibia in extension, and the extension gap.

One embodiment of the present invention is a device (spacing means) for assisting prosthetic knee surgery by maintaining a correct flexion gap between the femur and tibia while the knee is in flexion, said device comprising at least one elongate member (18) of dimensions for introduction through a hole (10, 11) that passes from the anterior (14) end of a femoral condyle (5, 6) through to the posterior (15) end of said condyle (5, 6), which member is provided with an adjustable protrusion configured to protrude from the posterior (15) end of said condyle (5, 6) by an amount at least equal to the flexion gap (4).

Another embodiment of the present invention is a device as defined above wherein:
said elongate member is a pin (18),
said adjustable protrusion is a threaded region (20) at least at one end of said pin (18), and the device further comprises a keeper (85) provided with a threaded hole (19) for engagement with the thread (20) of said pin (18), said keeper configured to abut with the posterior (15) end of said condyle (5, 6).

Another embodiment of the present invention is a device as defined above wherein:
said elongate member is a pin (18),
said adjustable protrusion is region provided with a plurality of inclined barbs (101), located at least at one end of the pin, which barbs are configured to fold back upon on contact with an entry side of the hole (10, 11), and open and abut against the posterior (15) end of said condyle (5, 6) at an exit side of the hole (10, 11).

Another embodiment of the present invention is a device as defined above wherein the number of elongate members is two.

Another embodiment of the present invention is an alignment device (26) for aligning a block for cutting the posterior (15) femoral condyles (5, 6) during prosthetic knee surgery, which device comprises:
(i) a securing means (23, 23') for temporary attachment to a fitted tibial plate (7), which securing means fixes the position and orientation of the alignment device (26) relative to the tibial plate (7),
(ii) a coupling means (24) for temporary attachment to a posterior femoral cutting block (29), which coupling means prevents rotation of the posterior femoral cutting block (29), around a z-axis, where the z-axis is parallel to the intermedular femoral axis, and
(iii) an extending means (25) joining (i) and (ii), which extending means is configured to adjust the distance between (i) and (ii) along a y-axis, where the y-axis is defined as being parallel to the intermedular tibial axis.

Another embodiment of the present invention is an alignment device (26) as defined above wherein the securing means comprises a pair of pins (23, 23') configured for insertion into a corresponding pair of holes (22, 22') present on the edge of the tibial plate (7).

Another embodiment of the present invention is an alignment device (26) as defined above wherein said coupling means permits displacement of the posterior femoral cutting block (29) parallel to the x-axis.

Another embodiment of the present invention is an alignment device (26) as defined above, wherein said coupling means is a finger-like protrusion having an upper surface disposed with a flat groove, which groove is configured to engage with a pointed ridge of a receiving elongate slot (30) present in said posterior femoral cutting block (29).

Another embodiment of the present invention is an alignment device (26) as defined above wherein said extending means (25) is connected to the coupling means (24) by way of a cylindrical coupling that permits rotation of the posterior femoral cutting block (29) around the y-axis.

Another embodiment of the present invention is an alignment device (26) as defined above wherein the extending means (25) comprises a rack-and-pinion assembly where the rack element (27) carries the coupling means (24), while the pinion (28) carries the securing means (23, 23'), or vice versa.

Another embodiment of the present invention is a posterior femoral cutting block (29) comprising one or more blade guides (31, 32), further comprising a receiving slot (30) configured to receive a coupling means (24) attached to an alignment device (26) as described above.

Another embodiment of the present invention is a posterior femoral cutting block (29) as defined above, wherein a plane of blade guide (31, 32) is aligned with the x-z plane, and set at an angle of between −10 and +10 deg around the x-axis.

Another embodiment of the present invention is a posterior femoral cutting block (29) as defined above, wherein the receiving slot (30) runs parallel to the blade guides (31, 32), and connects the front (33) of the block to the back (34).

Another embodiment of the present invention is a posterior femoral cutting block (29) as defined above, wherein said receiving slot (30) is wider than the coupling means (24), allowing the posterior femoral cutting block (29) to move parallel to the x-axis relative to the coupling means (24) where the x-axis is perpendicular to the y-z plane.

Another embodiment of the present invention is a posterior femoral cutting block (29) as defined above, further comprising an intramedular fermoral rod guide (35), which rod guide comprises an elongate slot (44) oriented perpendicular to said receiving slot (30), and is configured to receive an intramedular femoral rod, IM rod (38).

Another embodiment of the present invention is a posterior femoral cutting block (29) as defined above, wherein the rod guide (35) is configured to receive a sliding bushing (40), which bushing (40) is provided with a hole (41) through which the IM rod (38) passes.

Another embodiment of the present invention is a posterior femoral cutting block (29) as defined above, further comprising the bushing as defined above.

Another embodiment of the present invention is a posterior femoral cutting block (29) as defined above, wherein the central axis of said hole (41) crosses a transverse axis (B-B') of the bushing (40) by angle between −15 and 15 deg.

Another embodiment of the present invention is a posterior femoral cutting block (29) as defined above, comprising two or more holes (56, 57), the central axis of which lie in an axis parallel to the y-axis, configured to receive two or more attachment means (48, 48") of an anterior femoral cutting block (46) and distal femoral cutting block (50), such that a plane of the blade guide (47) of the anterior block (46) aligns with the x-z plane and a plane of the blade guide (51) of the distal block (50) aligns with the x-y plane.

Another embodiment of the present invention is a posterior femoral cutting block (29) as defined above, wherein said rod guide (35) is an elongate structure perpendicular to the width of the receiving slot (30) and disposed with one or more outer grooves (66) running in an axis parallel to the y-axis, said grooves configured to receive an attachment means (94, 95) of a posterior femoral cutting block (29).

Another embodiment of the present invention is an anterior femoral cutting block (46) as defined above disposed with a blade guide (47), said block provided with an attachment means (48', 48", 94, 95) for attaching to the posterior femoral cutting block (29), which means (48', 48", 94, 95) is configured to align a plane of the blade guide (47) with the x-z plane.

Another embodiment of the present invention is an anterior femoral cutting block (46) as defined above wherein said plane is set at an angle between −10 and +10 deg around the x-axis.

Another embodiment of the present invention is a distal femoral cutting block (50) disposed with a blade guide (51), said block provided with an attachment means (52, 55) for joining the block to the posterior femoral cutting block (29), which means (52, 55) is configured to align a plane of the blade guide (51) with an x-y plane.

Another embodiment of the present invention is a kit comprising one or more of the following:
- at least one device (spacing means) as defined above,
- an alignment device (26) as defined above,
- a posterior femoral cutting block as defined above,
- an anterior femoral cutting block (46) as defined above,
- a distal femoral cutting block (50) as defined above.

Another embodiment of the present invention is a kit as defined above, further comprising a tibial plate (7) disposed with a receiving slot for receiving the securing means (23, 23') of the alignment device (26) as defined above.

Another embodiment of the present invention is a kit as defined above, further comprising a knee prosthesis.

Another embodiment of the present invention is a method for performing replacement prosthetic knee surgery, after fitting a tibial plate (7) comprising the steps:
- tensioning the knee joint while in flexion, while the patella is in place to obtain or reproduce the correct flexion gap,
- maintaining the tension using an adjustable the spacing means between the fitted tibial plate (7) and the femur, and
- performing femoral bone cuts after the patella is moved to one side.

Another embodiment of the present invention is a method as defined above, further comprising the steps of:
- making a hole (10, 11) in each femoral condyle, which hole passes through the anterior region (14) of the femoral condyle and exits though the posterior end (15),
- inserting said spacing means through said holes (10, 11) so introducing said spacing means into the flexion gap while the patella is in place.

Another embodiment of the present invention is a method as defined above, wherein said spacing means is as defined above.

Another embodiment of the present invention is a method as defined above, further comprising the step of attaching a posterior femoral cutting block (29) to the tibial plate (7) using an alignment means which permits movements by the posterior femoral cutting block (29) along a y-axis, along an x-axis, and permits rotation about x- and y-axes relative to a static tibial plate, where the y-axis is parallel to the intermedular tibial axis, and the x-axis is perpendicular to the plane of the y- and z-axes, where the z-axis is parallel to the intermedular femoral axis, which step is applied after the patella is moved to one side.

Another embodiment of the present invention is a method as defined above, wherein said alignment means is an alignment device as defined above.

Another embodiment of the present invention is a method as defined above, further comprising the step of securing the posterior femoral cutting block (29) to the femur in an aligned position using pins (65', 65") inserted into the posterior femoral cutting block (29) and driven into the femur.

Another embodiment of the present invention is a method as defined above, wherein said posterior femoral cutting block is a device as defined above.

Another embodiment of the present invention is a method as defined above, further comprising the step of attaching an anterior femoral cutting block (46) disposed with a blade guide (47) to the posterior femoral cutting block (29), using a means which aligns the blade guide (47) with the x-y plane, and allows translational movement of the anterior femoral cutting block (46), along an axis parallel to the y-axis.

Another embodiment of the present invention is a method as defined above, wherein said anterior femoral cutting block is a device as defined above.

DETAILED DESCRIPTION OF THE INVENTION

Unless defined otherwise, all technical and scientific terms used herein have the same meaning as is commonly understood by one of skill in the art. All publications referenced herein are incorporated by reference thereto.

The articles "a" and "an" are used herein to refer to one or to more than one, i.e. to at least one of the grammatical object of the article. By way of example, "a pin" means one pin or more than one pin.

Throughout this application, the term "about" is used to indicate that a value includes the standard deviation of error for the device or method being employed to determine the value.

The recitation of numerical ranges by endpoints includes all integer numbers and, where appropriate, fractions subsumed within that range (e.g. 1 to 5 can include 1, 2, 3, 4 when referring to, for example, a number of pins, and can also include 1.5, 2, 2.75 and 3.80, when referring to, for example, an angle in degrees).

Reference is made in the description below to the drawings which exemplify particular embodiments of the invention; they are not at all intended to be limiting. The skilled person may adapt the device and substituent components and features according to the common practices of the person skilled in the art.

Figure 2:
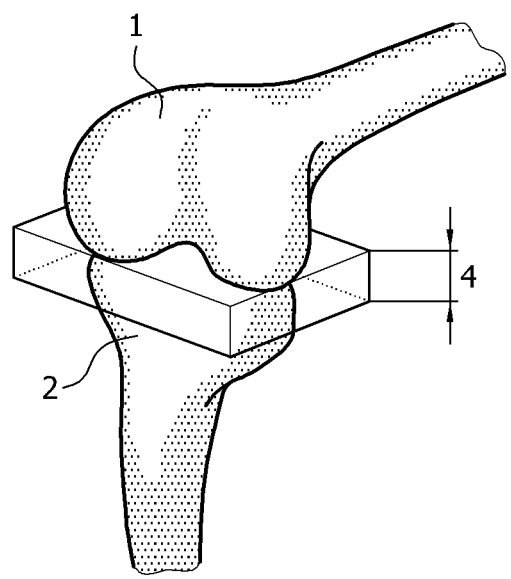
FIG. 2 depicts a three dimensional view of the femur and tibia in flexion, and the flexion gap.

The present invention relates to a method and device for providing accurate bone cuts during fitting of the femoral component of a knee prosthesis. With reference to FIGS. 1 and 2, the invention is based on avoiding the changes to the flexion gap 4 that arises when the patella 9 (knee cap) is moved to one side during femoral cutting, when the knee is in flexion. The inventors have found that if a spacing means is introduced between the femur 1 and tibia 2 while the patella 9 (FIG. 3) is in place, which spacing means maintains the distance between the femur 1 from the tibia 2 by an amount essentially equal to or greater than the required flexion gap 4, the femoral bone cuts made after the patella is moved to one side are so accurate that the soft tissue balancing is avoided altogether or reduced.

The present invention also relates to an alignment device for performing femoral bone cuts, which device attaches temporarily to a fitted tibial plate. The alignment device allows the surgeon accurately to cut the posterior femoral condyle to create the correct flexion gap 4 after fitting, to make a distal resection that maintains the correct extension gap 3 after fitting, and to make the required cut the anterior femoral condyle. By referencing the cuts to the tibial plate, the cuts are made with consideration to the femoral/tibial gaps.

Furthermore, the solid attachment by the present device to the tibial plate provides stable alignment of the cutting blocks. This is different from devices of the art which do not use the tibial plate as a reference or attach thereto, and thus rely more on the skill of the surgeon, on soft tissue balancing and post operative physiotherapy.

When the spacing means is combined with the alignment device, the inventors have found that subjects do not require such extensive post-operative physiotherapy as compared with prior art methods, and can be discharged from hospital within a few days. This contrasts with existing techniques and devices which normally require a long hospital stay, and several weeks of post-operative treatment for the subject to reach the same state. The faster recovery time reduces the cost of fitting a knee prosthesis due to less hospital overnight time; the risk of infection during hospitalisation is concomitantly reduced.

Spacing Means

Figure 3:
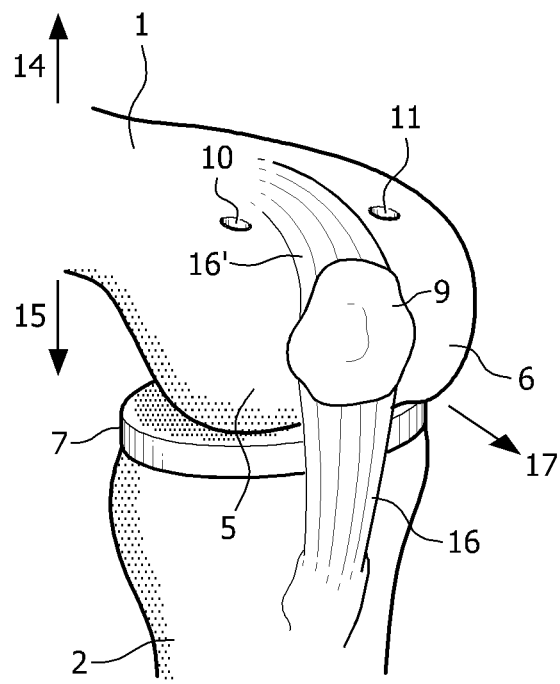
FIG. 3 shows a three dimensional view of the femur and tibia in flexion, where the femur is disposed with transcondylal holes, and where the patella is in place.
Figure 4:
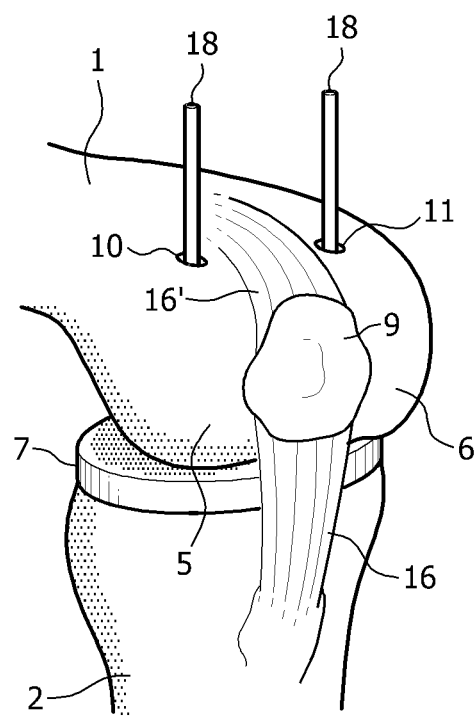
FIG. 4 shows a three dimensional view of the femur and tibia in flexion, spacing pins are placed in the transcondylal holes, and where the patella is in place.

Reference is made to FIGS. 3 and 4 in the foregoing description. One embodiment of the invention is a spacing means, configured for introduction through the anterior 14 region of a femoral condyle 5, 6, which spacing means maintains and/or adjusts the tension between the posterior femoral condyles 5, 6 and a fitted tibial plate 7 while the knee is in flexion. The spacing means is generally adjusted to maintain the flexion gap 4. The spacing means preferably comprises at least one elongate member 18 of dimensions for introduction through a hole 10, 11 that passes from the anterior 14 end of a femoral condyle 5, 6 through to the posterior 15 end of said condyle 5, 6. The means further comprises an adjustable protrusion that is configured to protrude from the posterior 15 end of said condyle 5, 6 by an amount at least equal to the flexion gap 4. Thus, when placed in the hole 10, 11, each adjustable protrusion can contact the tibial plate 7. By adjusting the distance by which the protruding part extends from the posterior 15 end of said condyle 5, 6, the required gap between the femoral condyles 5, 6 and tibial plate 7 can be obtained and/or maintained. Preferably, the number of spacing means is two, one for a hole in each of the condyles. Preferably two holes are made such that an imaginary line drawn between the two holes is essentially at right angles to the intramedular femoral axis. Preferably the passage of each hole is essentially perpendicular to the intramedular femoral axis. Preferably each hole is placed in the middle of each femoral condyle.

According to one aspect of the invention, the above mentioned spacing means comprises:

an elongate member that is a cylindrical pin configured for introduction through a hole 10, 11 that passes between the anterior 14 region of a femoral condyle 5, 6 and the posterior 15 end of said condyle 5, 6, an adjustable protrusion which is a serrated region, located at least at one end of the pin, and a keeper provided with a hole and ratchet mechanism for engagement with the thread of said pin, said keeper configured to attach and abut with the posterior 15 end of said condyle 5, 6. The body of the keeper is sufficiently thin so as not to occupy the entire flexion gap.

In this configuration, the spacing means operates in a similar manner to a cable tie in that the movement of the serrated region is locked in one direction by the rachet.

Figure 5A:
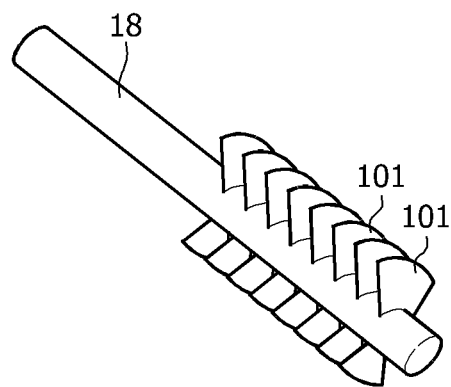
FIG. 5A shows a three dimensional view of a barbed pin.
Figure 5B:
FIG. 5B shows a profile view of the barbed pin of FIG. 5A.

According to one aspect of the invention, the above mentioned spacing means comprises:

an elongate member that is a cylindrical pin 18 (FIGS. 5A and 5B) configured for introduction through a hole 10, 11 that passes between the anterior 14 region of a femoral condyle 5, 6 and the posterior 15 end of said condyle 5, 6, an adjustable protrusion which is region provided with a plurality of inclined barbs 101, located at least at one end of the pin, which barbs are configured to fold back upon on contact with the entry side of the hole 10, 11, and open and abut against the posterior 15 end of said condyle 5, 6 at the exit side of the hole 10, 11. The barbed region allows the surgeon to obtain and main the correct flexion gap, simply by applying pressure on the elongate member in the direction required. As the spacing means may not be withdrawn, it may be made from a biodegradable material such as a described below. The adjustable protrusion part may be removed by cutting or snapping off. The barbs 101 are preferably an array of inclined fins. Barbs 101 which restrict a movement of an object in a cavity in one direction are well known in the art e.g. from rawlplugs, from nature; the skilled person may readily provide a spacing means described herein with suitable barbs.

Figure 6A:
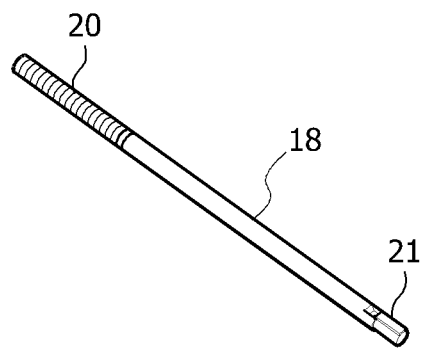
FIG. 6A shows a three dimensional view of a spacer pin.
Figure 6B:
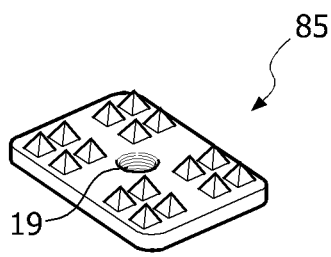
FIG. 6B shows a three dimensional view of a keeper.

According to a preferred aspect of the invention, the spacing means comprises:

an elongate member that is a cylindrical pin 18 (FIG. 6A) configured for introduction through a hole 10, 11 that passes between the anterior 14 region of a femoral condyle 5, 6 and the posterior 15 end of said condyle 5, 6, an adjustable protrusion which is a threaded region 20, located at least at one end of the pin 18, and a keeper 85 (FIG. 6B) provided with a threaded hole 19 for engagement with the thread of said pin, said keeper configured to abut with the posterior 15 end of said condyle 5, 6. The body of the keeper is sufficiently thin so as not to occupy the entire flexion gap.

The pin 18 may apply the necessary tension between the femoral condyles 5, 6 and tibial plate 7 when the pin is rotated; the distance between the end of the pin and the engaged keeper extends or reduces during pin rotation. The necessary tension is generally that require to maintain the flexion gap 3 or enlarge it. Once the required flexion gap is maintained, the patella 9 can be moved aside, and the cuts made to the femoral condyles 5, 6 in the knowledge that the flexion gap 3 will be maintained while the surgeon measures the joint for making the necessary cuts. Optionally, the pin 18 can be provided with a coupling 21 for a tool that facilitates rotation, such as an hexagonal end (shown in FIG. 6A), or a hole.

By configuring the spacing means to enter the anterior 14 region of a femoral condyle, the patella 9 can remain fully in place during tensioning. This overcomes the problems of the prior art, where tensioning takes place through attachment of a device to the distal end 17 of the femur 1. This necessitates removal of the patella 9 to gain access to an attachment point. However, once the patella 9 is removed, tensioning is made without the constraints of patella 9 ligaments 16, 16', and the skill and experience of the surgeon become crucial to compensate for the loss of tension by said ligaments 16, 16' and to achieve satisfactory results, unlike the present invention. With this invention the spacing means overcomes the balance problem by avoiding the need to remove the patella 9.

The spacing means can be made from any material having suitable compression strength, and meeting the requirements for surgical instrument biocompatibility. Such materials include, for example, stainless steel and titanium. According to one aspect of the invention, the pin and keeper arrangement is biodegradable, in which case, it is may be made from biodegradable alloys (e.g. magnesium alloys) or polymer (e.g. polyglycolide (PGA), polylactide (PLA), poly(epsilon-caprolactone), poly(dioxanone), poly(lactide-co-glycolide)), or a combination of these.

Alignment Device

Figure 7:
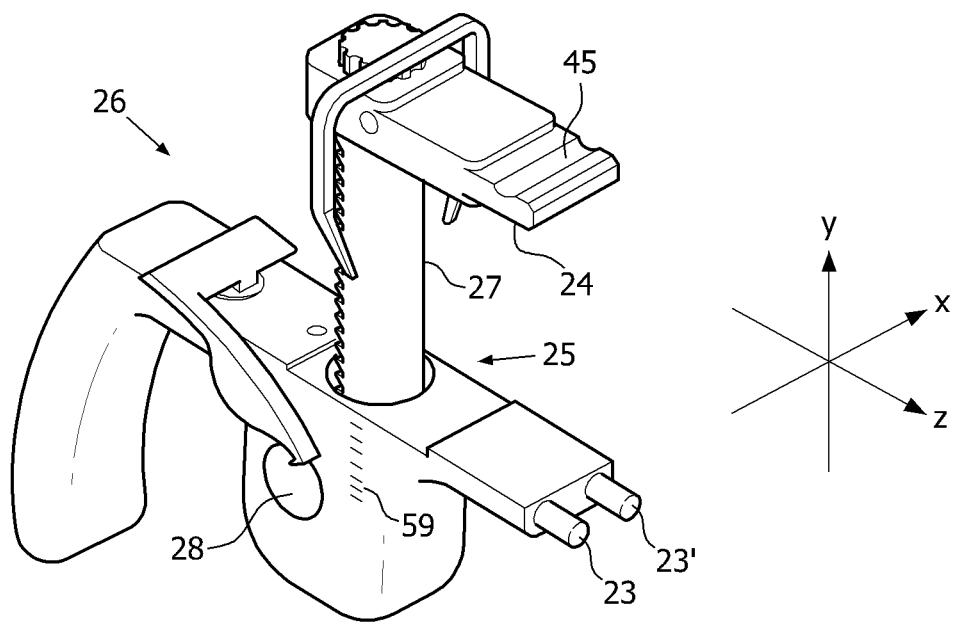
FIG. 7 shows a three dimensional view of an alignment device of the present invention.
Figure 8:
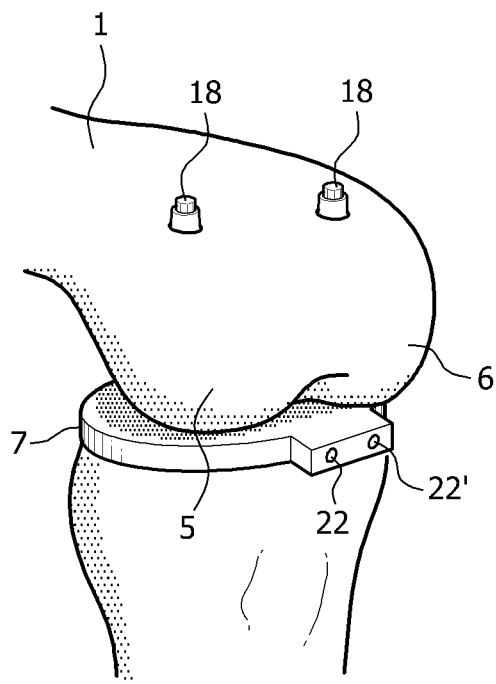
FIG. 8 shows a three dimensional view of the femur and tibia in flexion, where the femur is disposed with spacing means, and the tibial plate is fitted.

The following description are made with reference to FIGS. 7 and 8. Another embodiment of the present invention is an alignment device 26 for cutting the posterior femoral condyles 5, 6, which device comprises:
(i) a securing means 23, 23' for temporary attachment to a fitted tibial plate 7,
(ii) a coupling means 24 for temporary attachment to posterior femoral cutting block 29,
(iii) an extending means 25 joining (i) and (ii), which extending means is configured to adjust the distance along the y-axis between (i) and (ii), where the y-axis is defined as being parallel to the intermedular tibial axis.

Securing Means

The securing means 23, 23' can be any which allows the alignment device 26 to attach to the tibial plate 7, and which fixes the position and orientation of the alignment device 26 relative to the tibial plate 7. Thus, any movement by the tibial plate 7 or tibia 2 is transmitted to the alignment device 26, and vice versa. The securing means can be a protrusion shaped for insertion into a corresponding slot present on the edge of the tibial plate 7. Preferably the securing means comprises a pair of pins 23, 23' configured for insertion into a corresponding pair of holes 22, 22' present on the edge of the tibial plate 7. Preferably, the securing means 23, 23' orients the alignment device on the tibial plate 7 such that extending means 25 adjusts along the y-axis. Preferably the securing means 23, 23' orients alignment device such that the longitudinal axis of the extending means is at 85, 86, 87, 88, 89, 90, 91, 92, 93, 94 or 95 deg to the tibial plate, or at an angle between any two of the aforementioned angles. Preferably, it is at 90 deg.

Coupling Means

The coupling means 24 is any that allows the temporary attachment of a posterior femoral cutting block 29 so that said block is positioned at least approximately to cut the posterior femoral condyles after attachment. Generally the coupling means 24 is a finger like protrusion that can couple with a receiving elongate slot on the posterior femoral cutting block 29. The coupling means brings the posterior femoral cutting block 29 in parallel alignment with the tibial plate (see also FIG. 10). It may prevent free rotation (i.e. prevent rolling) of the posterior femoral cutting block 29, around the z-axis, where the z-axis is parallel to the intermedular femoral axis. It may, however, permit limited rotation of the cutting block 29 about the x-axis, i.e. it may allow tilting (pitching) of the block 29 to provide angled cuts. It may also permit limited rotation of the posterior femoral cutting block 29 around the y-axis, i.e. it may allow the cutting block to yaw. The coupling means may permit lateral (side-to-side) displacement of the posterior femoral cutting block 29 relative to the tibial plate i.e. movement parallel to the x-axis, where the x-axis is perpendicular to the plane of the y and z-axis. In one embodiment, the coupling means 24 is a finger-like protrusion with a flat surface which surface contacts a receiving elongate slot 30 in the posterior femoral cutting block 29. In a preferred embodiment, the coupling means 24 is a finger-like protrusion having an upper surface disposed with a flat groove 45, which groove 45 engages a pointed ridge present in the receiving elongate slot 30. The ridge and groove arrangement allows the cutting block 29 to pivot around the x-axis relative to the alignment device 26. The elongate slot 30 is preferably wider than the coupling means 24, so the posterior femoral cutting block 29 can move laterally (parallel to the x-axis) relative to the coupling means 24. A locking mechanism may be present in the posterior femoral cutting block 29 to secure the alignment device 26, which mechanism may lock a preferred lateral placement.

Extending Means

The extending means 25 adjusts the distance between the coupling 23, 23' and securing means 24 along a linear axis. The linear axis of the adjustment is normally parallel to the y-axis. Preferably, the extending means 25 prevents any other displacement or rotation movement between the coupling 23, 23' and securing means 24. However, it may permit a step-wise rotation of the coupling means 23, 23' relative to the securing means 24 by way of serrated joints as explained further below. The extending means 25 positions the posterior femoral cutting block 29 over the posterior femoral condyles. By extending or contracting the means 25, the surgeon can precisely select the amount of bone to remove from the posterior surface of the femoral condyles.

The extending mechanism of the extending means 25 can be any. It should enable a precise control of the distance between the tibial plate 7 and the posterior femoral cutting block 29, which distance can be locked during cutting.

Figure 12A:
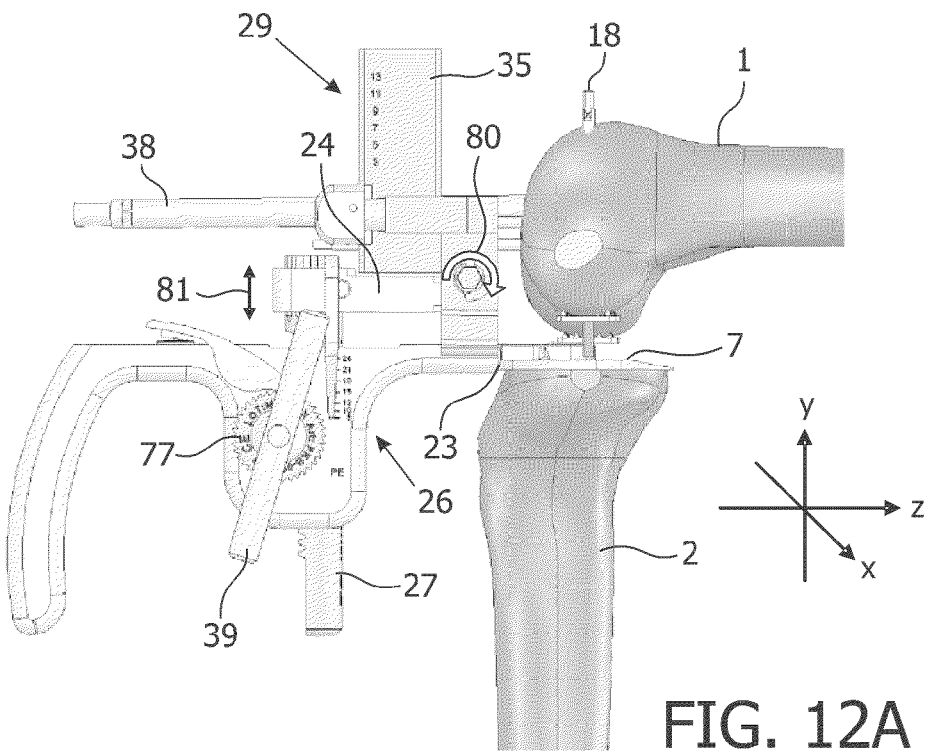
FIG. 12A and B shows a three dimensional view of an alignment device coupled to a posterior femoral cutting block and secured to a tibial plate; 12A is a side view, 12B is a front view.
Figure 12B:
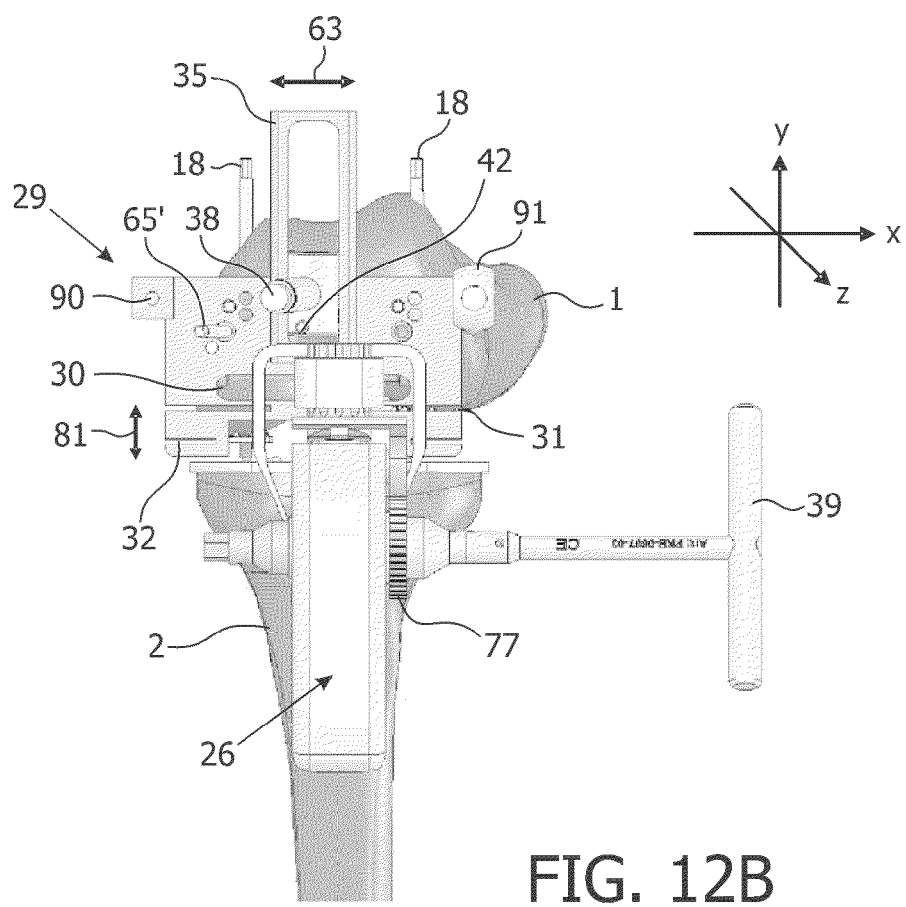
Figure 19:
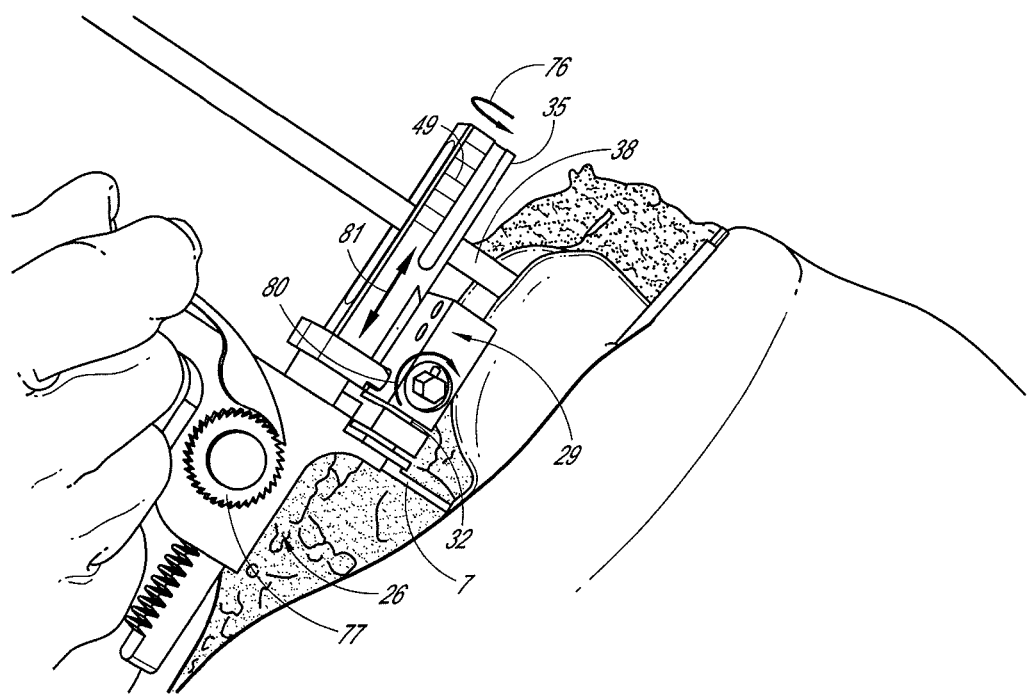
FIG. 19 shows a photograph of an alignment device coupled to a posterior femoral cutting block and secured to a tibial plate during surgery.

According to a preferred embodiment of the invention, the extending means comprises a rack-and-pinion assembly as shown in FIG. 7. The rack element 27 may carry the coupling means 24, while the pinion part (obscured in the FIG. 28 may carry the securing means 23, 23', or vice versa. The rack element 27 is normally oriented parallel to the y-axis. The invention also includes variants where rack element is set at an angle to the y-axis. Rotation of the pinion 28, for example by the insertion of a turning handle 39 brings about the required change in distance between the coupling means 24 and securing means 23, 23'. Other elements can be present within the extending means, which allow fine control of pinion rotation e.g. a rachet system 77 as seen in FIGS. 12A, 12B, and 19.

In another preferred embodiment, the extending means 25 is connected to the coupling means 24 by way of a cylindrical coupling. The cylindrical coupling comprises a cylindrical protrusion in either the extending means 25 or coupling means 24 that can be received by a cylindrical hole in the other component. This arrangement allows the coupling means 24 to rotate (FIG. 19, 76) around the extending means. This will permit the posterior femoral cutting block 29 to yaw i.e. to rotate about the y-axis. The cylindrical coupling may further be provided with a locking means to hold securely the desired yaw position of the cutting block.

Figure 9:
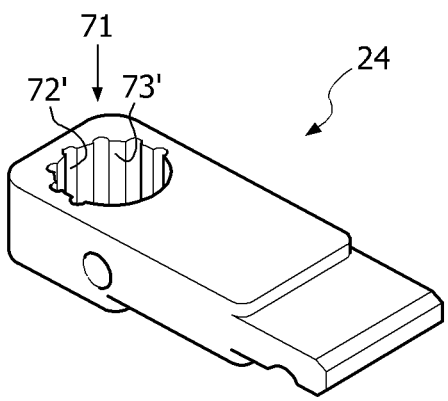
FIG. 9 shows a three dimensional view of a coupling means of an alignment device disposed with a serrated cylindrical hole.
Figures 10A, 10B:
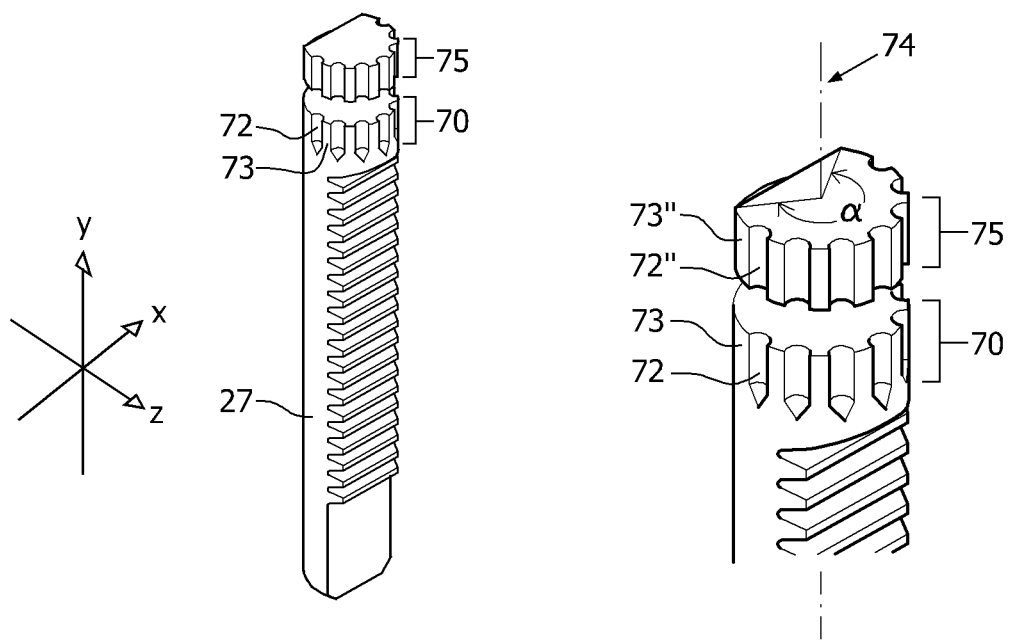
FIG. 10A shows a three dimensional view of a rack element of an alignment device, provided with a serrated cylindrical protrusion.
FIG. 10B shows a detailed view of the serrated cylindrical protrusion of FIG. 10A.

In another preferred embodiment of the invention, the cylindrical protrusion 70 is present on the rack element 27 of the extending means 24. Preferably, the cylindrical protrusion 70 is at least partly serrated as shown in FIGS. 10A and 10B. It may be provided with regularly spaced grooves 72 and ridges 73 that run parallel to the longitudinal axis 74 of the cylindrical protrusion 70. The cylindrical hole 71 is reciprocally serrated as shown in FIG. 9, such that the respective ridges 73, 73' and grooves 72, 72' interlock when the coupling means 24 is connected to the extending means 25. The arrangement prevents the posterior femoral cutting block 29 from freely rotating about the y-axis owing to the interlocking grooves and ridges, but allows the desired orientation about the y-axis to be chosen by removing and repositioning the coupling means 24.

In the embodiment shown in FIGS. 10A and 10B, the cylindrical protrusion is extended along its longitudinal axis by a serrated upper 75 element, having an incomplete cylindrical surface. In other words, the round surface of the cylinder is disposed less than 360 deg around its central axis 74. In FIG. 10B, the cylinder is disposed by angle alpha around the central axis 74. Angle alpha may be 100, 110, 120, 130, 140, 150, 160, 170, 180, 190, 200, 210, 220, 230, 240, 250, 260, 270, 280, 290, 300, 310, 320, 330, 340 deg, or a value in the range between any two of the aforementioned values.

The grooves 72" and ridges 73" of the upper element 75 preferably align with the ridges and grooves of the cylindrical protrusion 70.

Because the cylinder is incomplete in the upper element 75, the coupling means 24 can be engaged with the serrations (i.e. grooves 72" and ridges 73") of the upper element 75 by moving the coupling means 24 towards the serrated part of the upper element 75. The coupling means 24 can also by easily released by moving coupling means 24 away from the serrated part of the upper element 75. The movement required temporarily to release or lock the coupling means 24 is a convenient translation movement within the x-z plane, as opposed to an up-down movement along the y-axis. Once the correct angle with respect to the y-axis has been obtained, the coupling means 24 can be pushed down to engage with the full cylindrical protrusion 70.

The alignment device 26 is temporarily attachable to both the tibial plate 7 and posterior femoral cutting block 29. Once the cutting block is properly aligned, the alignment device 26 can be removed, leaving the cutting block in place, held, for example, by securing pins driven into the femur. With the removal of the alignment device, the surgeon's view and freedom of movement is unobstructed, so enabling efficient resectioning using the mounted posterior femoral cutting block 29.

Tibial Plate

The tibial plate has the elements of a conventional tibial plate, in addition to a receiving slot on the perimeter edge. The receiving slot receives the securing means 23, 23' of the alignment device 26. This allows the alignment device 26 to attach to the tibial plate 7, and to fix the position and orientation of the alignment device 26 relative to the tibial plate 7.

Thus, any movement by the tibial plate 7 or tibia 2 is transmitted to the alignment device 26, and vice versa. The receiving slot can be any slot for receiving a corresponding protrusion present on the alignment device. Preferably the tibial plate comprises a pair of holes 22, 22' present on the edge of the tibial plate 7 configured to receive a corresponding pair of pins 23, 23' present on the alignment device 26.

Posterior Femoral Cutting Block

Reference is made in the following description to FIGS. 11A, 11B, 12A and 12B. The posterior femoral cutting block 29 is a typical surgical femoral cutting block comprising a plurality of blade guides 31, 32, for visual alignment of the block against the condyles and to receive and guide a cutting blade. As already described above, the posterior femoral cutting block 29, also comprises a receiving slot 30 that receives the coupling means 24 attached to the alignment device 26. The receiving slot 30 preferably runs parallel to the blade guides in the x-axis direction, connecting the front 33 of the block to the back 34.

In additional to the receiving slot 30, the cutting block 29 may comprise an intramedular fermoral rod guide 35. Said rod guide 35 comprises an elongate slot 44 oriented perpendicular to the aforementioned receiving slot 30, configured to receive an intramedular femoral rod (IM rod) 38. The IM rod 38 passes through said slot. The IM rod 38 and rod guide 35 provide additional stabilisation to the cutting block 29 during alignment. The rod guide 35 permits upward 36 or downward 37 movement of the IM rod-mounted cutting block 29 during alignment, in concert with the extension or contraction of the extending means 25. An advantage of allowing the cutting block 29 to move laterally (parallel to the x-axis) relative to the coupling means 24 is the that the IM rod can be mounted by the cutting block 29 even when the coupling means 24 does not align with the IM rod 38.

FIGS. 12A and 12B show the posterior femoral cutting block 29 attached to the alignment device 26 which in turn is attached to the tibial plate 7. The alignment device moves along the y-axis as indicated by reference sign 81 in FIGS. 12A and 12B, by turning rachet 77 using handle 39. This allows alignment of posterior femoral cutting block 29 on the femur 1, relative to the tibial plate 7 or tibia 2. The posterior femoral cutting block 29 may pitch i.e. pivot around the x-axis in a limited manner as indicated by reference sign 80. The posterior femoral cutting block 29 may also be displaced along the x-axis relative to the tibial plate 7 or tibia 2, as indicated by reference sign 63. The posterior femoral cutting block 29 may also rotate around the y-axis relative to the tibial plate 7 or tibia 2 (see FIG. 19, reference sign 76). Thus the combination of the posterior femoral cutting block 29 attached to the alignment device 26 in situ permits precise control and movement of posterior femoral cutting block 29 along and around several axis, permitting the surgeon to find the precise alignment relative to the tibia. Once aligned, the posterior femoral cutting block 29 may be secured on the femur using one or more pins 65'.

Figure 23:
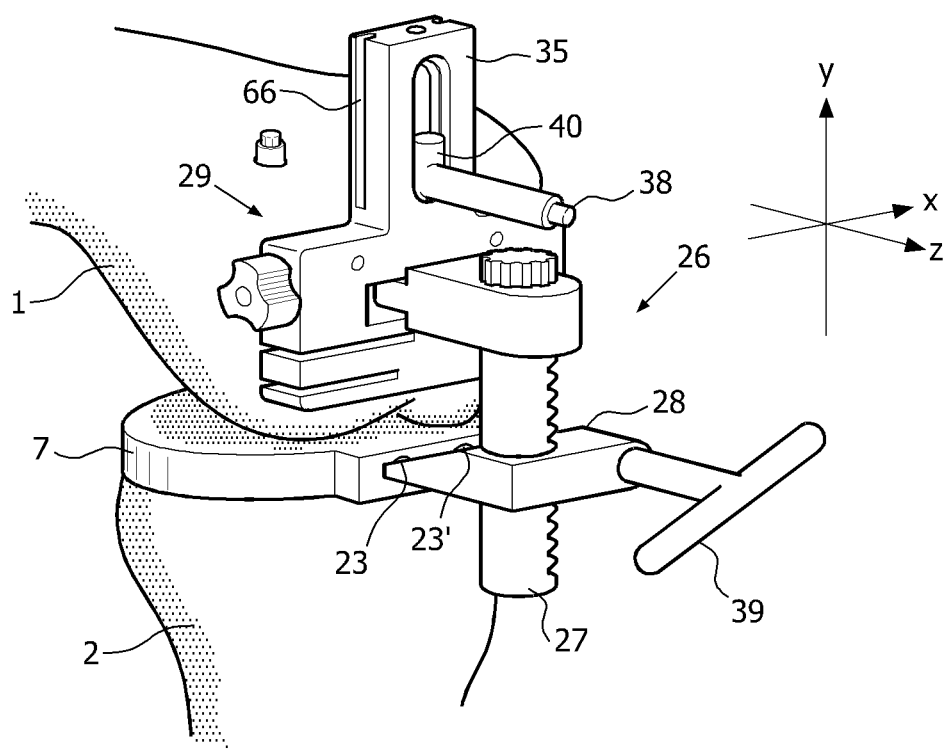
FIG. 23 shows a three dimensional view of an alternative alignment device attached to a posterior femoral cutting block.

A further embodiment of the present invention, depicted in FIG. 23, is a posterior femoral cutting block 29, wherein said rod guide 35 is an elongate structure perpendicular to the width of the receiving slot 30 and disposed with one or more outer grooves 66 running in an axis parallel to the y-axis, said grooves configured to receive an attachment means 94, 95 of a posterior femoral cutting block 29 (see below).

The grooves 66 allow the posterior femoral cutting block 29 to attach securely to the anterior femoral cutting block 46. When the attachment means 94, 95 comprises a pair of arms which locate closely with the groove, permitting the attachment means 94, 95 to move up and down, in a direction parallel to the y-axis. The arms can allow translational movement of the anterior femoral cutting block 46 along the rod guide 35, along an axis parallel to the y-axis. They also prevent other translations or rotations of the anterior femoral cutting block 46.

According to one aspect of the invention, the rod guide 35 acts as a housing for a sliding bushing 40 (FIGS. 13A to 13D), which bushing 40 is provided with a hole 41 through which the IM rod 38 passes. The bushing 40 fits tightly in the rod guide 35, while permitting free upward 36 or downward 37 movement by the bushing 40. The bushing may be disposed with a protrusion 42, which seats in one of the slots 44 present in the rod guide 35. The slot-seated protrusion prevents free rotation of a cylindrical bushing 40, so the bushing hole 41 is always aligned with the rod guide slot 44. This means the surgeon is not burdened with rotating a cylindrical bushing 40 in the rod guide 35 to find the hole 41. It also allows the surgeon to orient the bushing correctly to obtain the indicated angle. The protrusion 42 may be sufficiently narrow to permit a limited rotation by the bushing in the rod guide 35; this would allow some yawing by a posterior femoral cutting block 29 as described below and as indicated in FIG. 19, 76. The bushing hole 41 couples tightly with the IM rod 38.

The bushing hole 41 passes in the direction of the transverse axis of the bushing 40; the transverse axis (B-B', FIG. 13A) is perpendicular to the longitudinal (A-A' axis, FIG. 13B to 13C). According to one aspect of the invention, the central axis of the hole 41 is aligned with the transverse axis B-B' of the bushing 40. According to another aspect of the invention, the axis of the central axis of the hole crosses the transverse axis B-B' of the bushing 40 at an angle of 0, 1, 2, 3, 4, 5, 6, 7, 8, 9, 10, 11, 12, 13, 14 or 15 deg, or an angle in between any two of the aforementioned angles. For the required angle, a unique bushing 40 may be provided. Examples of separate bushing are shown in FIG. 13B (hole 41' at 0 deg), 13C (hole 41" at 3 deg) and 13D (hole 41''' 5 deg). To achieve the angles of −1, −2, −3, −4, −5, −6, −7, −8, −9, −10, −11, −12, −13, −14 or −15 deg, the bushing 40 may be inserted into the rod guide 35 in the opposing direction i.e. rotated 180 deg around axis A'A'. Alternatively, when a bushing cannot be rotated, the aforementioned negative angles may also be provided by virtue of separate bushings. A range of angles provided by a plurality of bushings 40 gives the surgeon the choice to fine tune the cutting angle.

Figure 11A:
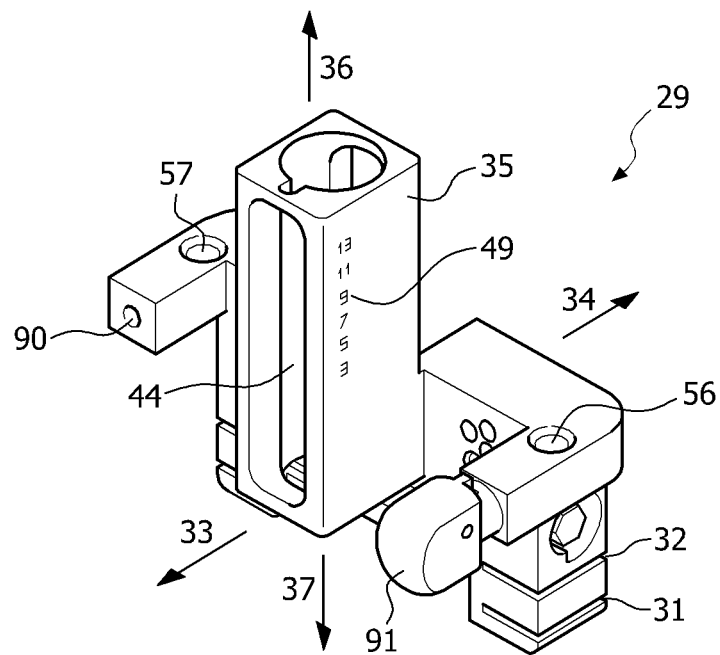
FIG. 11A shows a three dimensional view of a posterior femoral cutting block according to the invention.
Figure 11B:
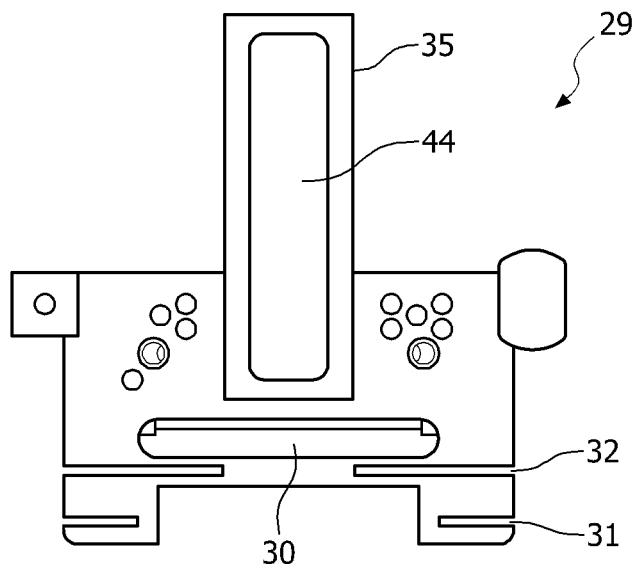
FIG. 11B shows a front elevation view of the posterior femoral cutting block of FIG. 11A.
Figure 15:
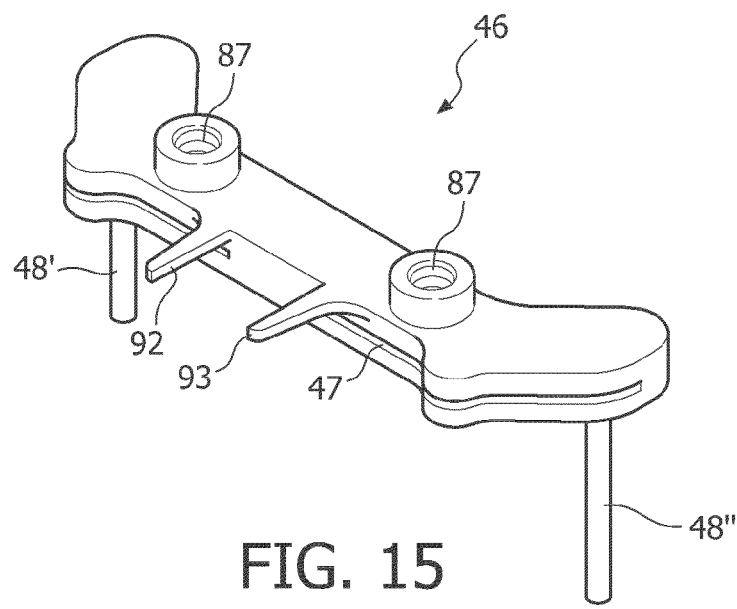
FIG. 15 shows a three dimensional view of an anterior femoral cutting block.
Figure 17:
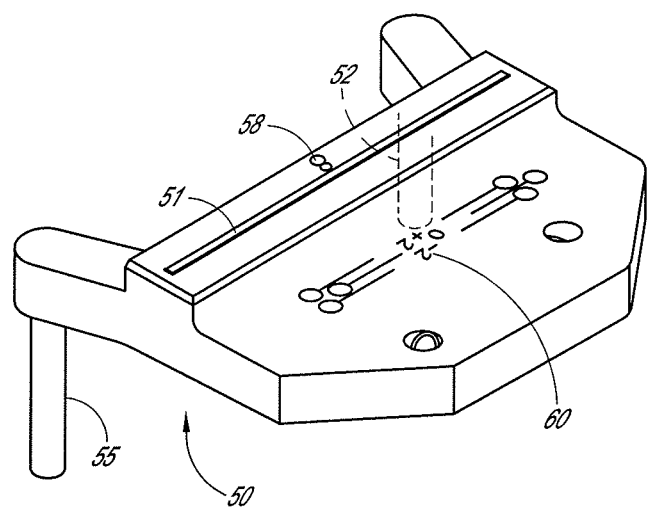
FIG. 17 shows a three dimensional view of a distal femoral cutting block.

A further embodiment of the present invention is a posterior femoral cutting block 29, disposed with one or more holes 56, 57 the central axis of which lies in an axis parallel to the y-axis (FIG. 11A). Said holes may be configured to receive an attachment means 48', 48" of an anterior femoral cutting block 46 (FIG. 15). Said holes may also be configured to receive an attachment means 52, 55 of an distal femoral cutting block 50 (FIG. 17). Preferably there are two holes located either side of the rod guide 35. Preferably the holes are cylindrical.

The holes allow the posterior femoral cutting block 29 to attach securely to the anterior femoral cutting block 46. When the attachment means 48', 48" is rod shaped as shown in FIG. 15, it may couple closely with the walls of the hole, permitting the attachment means 48', 48" to move up and down, in a direction parallel to the y-axis. The position of the anterior femoral cutting block 46 on the posterior femoral cutting block 29 may be locked by means of a threaded tightening bolt 88 that contacts the attachment means 48', 48" upon tightening through a threaded hole 90. Alternatively or in addition, the position of the anterior femoral cutting block 46 on the posterior femoral cutting block 29 may be locked by means of a sprung bolt that can releasably contact the attachment means 48', 48". The sprung bolt can be engaged or retracted by, for example, turning a knob 91. The sprung bolt allows the surgeon to adjust finely the position of the anterior femoral cutting block 46 prior to locking the final position with the tightening bolt.

The posterior femoral cutting block 29 is temporarily attachable to the alignment device 26. Once the cutting block is properly aligned, the alignment device 26 can be removed, leaving the cutting block in place, held, for example, by securing pins driven into the femur. For this purpose, the posterior femoral cutting block 29 may be provided with one or more holes running from the front 33 to the back 34 of the block through which securing pins can be inserted and driven in to the femur. With the removal of the alignment device, the surgeon's view and freedom of movement is unobstructed, so enabling efficient resectioning using the mounted posterior femoral cutting block 29.

One preferred embodiment of the invention is a posterior femoral cutting block 29 as described above comprising two or more holes 56, 57 the central axis of which lies in an axis parallel to the y-axis. The holes are configured to receive two or more attachment means 52, 55 of a distal femoral cutting block 50 such that a plane of the blade guide 51 of the distal block 50 is aligned with the x-y plane. The plane of a blade guide is the plane adopted by a blade when inserted into a blade guide. The same holes may also be configured to receive two or more attachment means 48', 48" of an anterior femoral cutting block 49 such that a plane of the blade guide 47 of the anterior block 46 is aligned with the x-z plane.

The plane of blade guides 31, 32 of the posterior femoral cutting block 29 may or may not be exactly parallel with the blade guide 47 of the anterior femoral cutting block 46. Often the prosthesis will fit onto a femur head where the anterior and posterior femoral cuts are angled in a wide V-shape. To achieve this, the planes of the blade guides of the anterior 49 and posterior 29 femoral cutting blocks may be aligned with the x-z plane, but set at an angle thereto around the x-axis.

In one embodiment of the invention, the plane of a blade guide 31, 32 of the posterior femoral cutting block 29 is aligned with the x-z plane, and set at an angle of −10, −9, −8, −7, −6, −5, −4, −3, −2, −1, 0, 1, 2, 3, 4, 5, 6, 7, 8, 9, 10 deg around the x-axis.

The combination of the alignment device 26 and the cutting block 29 as described herein allows the surgeon to align precisely the cutting block in two critical ways: laterally along the y-axis and according to an angle of rotation around the x-axis. No other adjustment is necessary as the inventors have found. The invention provides the surgeon with an accurate and convenient tool for accurately resection the femur.

Other Cutting Blocks

The posterior femoral cutting block 29 being accurate placed, acts as a referencing block for aligning the other cutting blocks used during knee prosthetic surgery, namely the anterior femoral cutting block 46, and the distal femoral cutting block 50.

Anterior Femoral Cutting Block

Reference is made in the following description to FIGS. 14A to 14D and 15. During prosthetic knee surgery, a cut to the bone is made parallel to the posterior femoral cut i.e. an anterior femoral cut. Accordingly, the present invention provides an anterior femoral cutting block 46 (FIG. 15) disposed with a blade guide 47, said block provided with an attachment means 48', 48" for attaching to the posterior femoral cutting block 29, which means 48', 48" is configured to align the blade guide 47 parallel with the blade guides 32 of the posterior femoral cutting block 29.

According to a preferred embodiment of the invention, the anterior femoral cutting block 46 comprises one or more attachment means 48, 48" which are configured to couple with one or more reciprocally positioned holes 56, 57. The attachment means 48', 48" may be rod shaped as shown in FIG. 15, which allows a close couple with the walls of the hole, permitting the attachment means 48', 48" to move up and down, in a direction parallel to the y-axis within the hole. It may also prevent other translations or rotations of the anterior femoral cutting block 46. Optionally, the attachment means 48', 48" can be disposed with a locking mechanism that holds the anterior femoral cutting block 46 in place once the appropriate position along the y-axis is found. Preferably there are two attachment means, configured to couple with a reciprocating pair of holes located either side of the rod guide 35. Preferably an attachment means is a cylindrical rod.

Figure 14A:
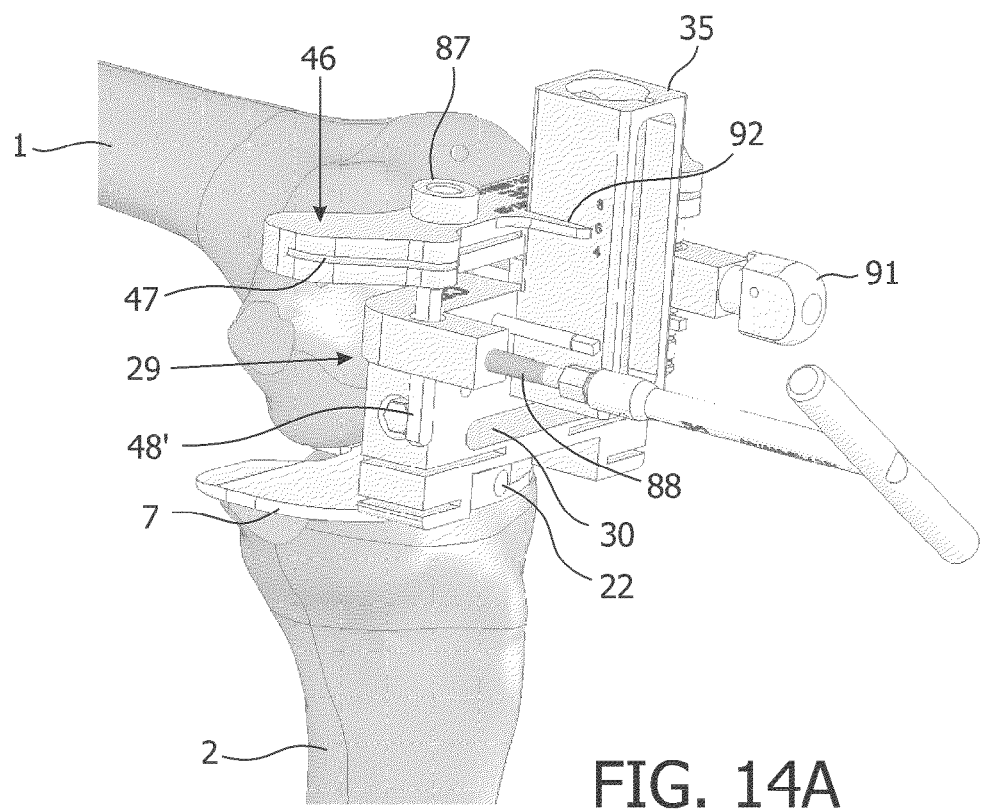
FIG. 14A shows a three dimensional view of a posterior femoral cutting block attached to a coupled to an anterior femoral cutting block during surgery.
Figure 14B:
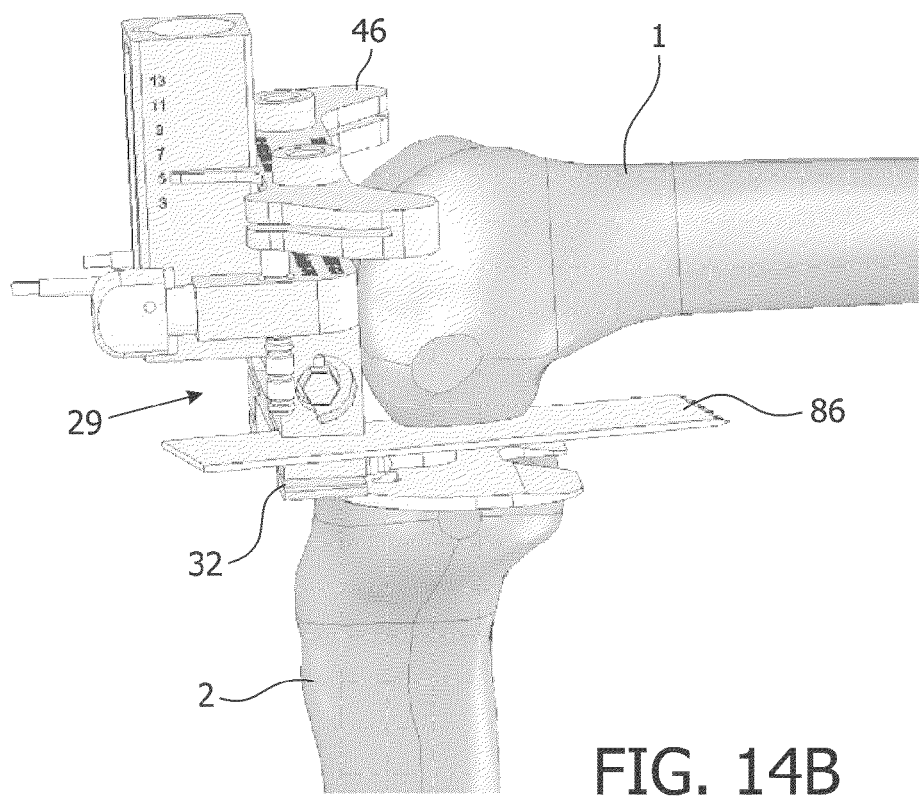
FIG. 14B shows the same device as FIG. 14A, including cutting the posterior end of the femor head.
Figure 14C:
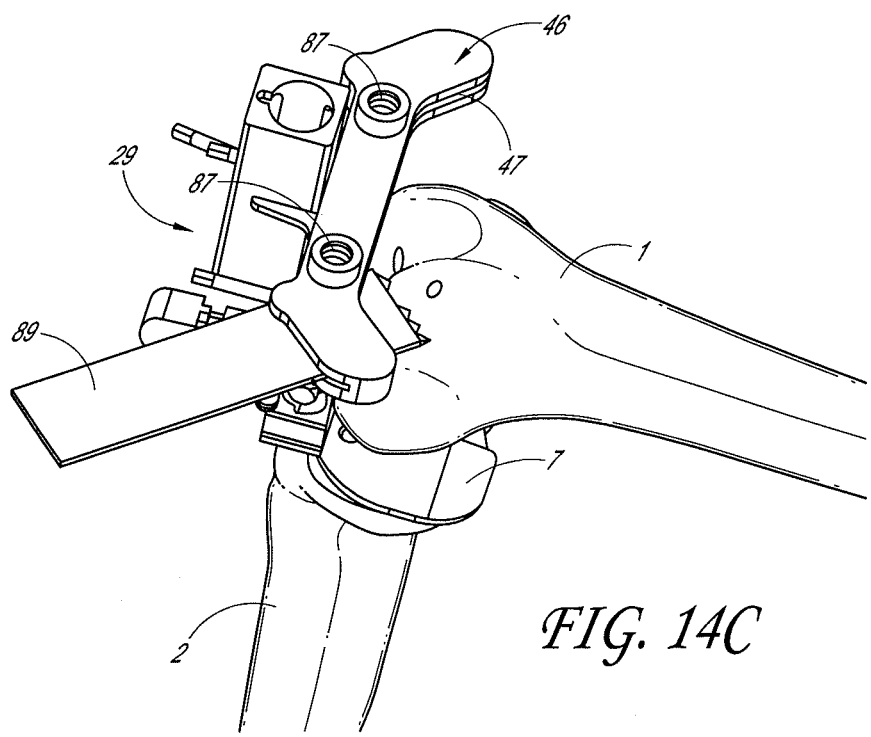
FIG. 14C shows the same device as FIG. 14A, including cutting the anterior end of the femor head.
Figure 14D:
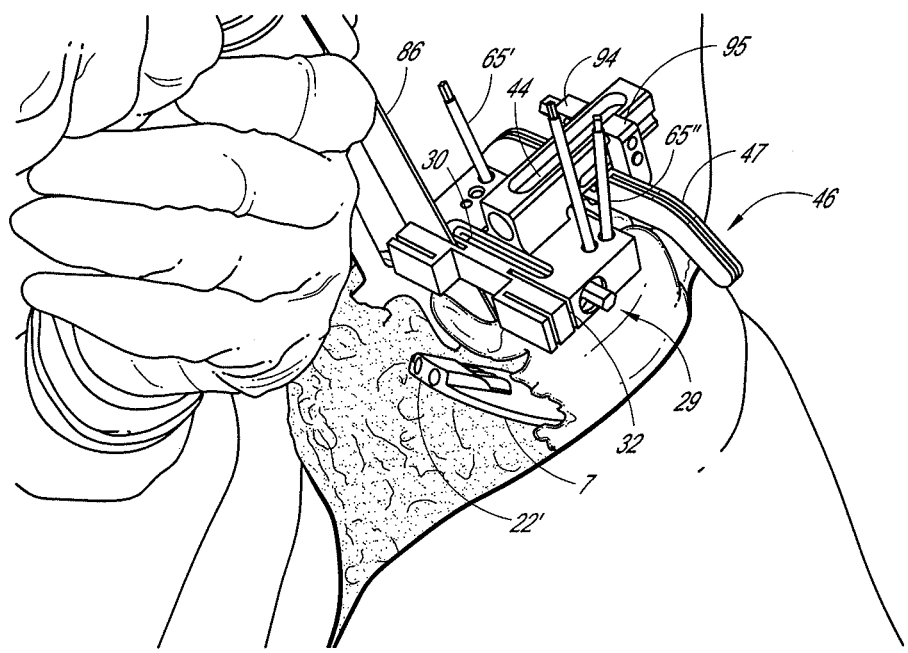
FIG. 14D shows a photograph of the device shown in FIG. 14A used during surgery, where the posterior end of the femor head is being cut.

FIG. 14A depicts an anterior femoral cutting block 46 attached in situ on a posterior femoral cutting block 29 via attachment means 48'. The anterior femoral cutting block 46 may be translated in a direction parallel to the y-axis, relative to the posterior femoral cutting block 29. The desired adjustment can be read using a distance reader 92 present on the anterior femoral cutting block 46 against a set of graduation present on the posterior femoral cutting block 29. Once the final position is obtained, theanterior femoral cutting block 46 can be locked using a threaded bolt 88. FIG. 14B depicts the anterior femoral cutting block 46 attached in situ on a posterior femoral cutting block 29 in situ, and the a cutting blade 86 making a section of a posterior femoral condyle. FIG. 14C depicts the anterior femoral cutting block 46 attached in situ on a posterior femoral cutting block 29 in situ, and the a cutting blade 86 making a section of a anterior femoral condyle. FIG. 14C is a photograph from an operation where the anterior femoral cutting block 46 attached in situ on a posterior femoral cutting block 29 in situ, and the a cutting blade 86 making a section of a posterior femoral condyle.

One embodiment of the present invention is an anterior femoral cutting block 46 disposed with one or more rod shaped attachment means 48, 48" which are configured to couple with one or more reciprocally positioned holes 56, 57 on the posterior femoral cutting block, permitting the anterior femoral cutting block 46 to move up and down, in a direction parallel to the y-axis.

According to a another embodiment of the invention, the attachment means 94, 95 (FIG. 14D) comprises two arms which grip the rod guide 35. Similarly, the rod guide 35 may be disposed with outer grooves 66 that receive the attachment means 94, 95 along which the anterior femoral cutting block 46 can be positioned in an axis parallel to the y-axis. The arms can allow translational movement of the anterior femoral cutting block 46 along the rod guide 35, along an axis parallel to the y-axis. The longitudinal axis of the arms 94, 95 are aligned with the x-y plane. They also prevent other translations or rotations of the anterior femoral cutting block 46. Optionally, the attachment means 94, 95 can be disposed with a locking mechanism that holds the anterior femoral cutting block 46 in place once the appropriate position along the y-axis is found.

The plane of blade guide 47 of the anterior femoral cutting block 49 may or may not be exactly parallel with the blade guides 31, 32 of the posterior femoral cutting block 29. Often the prosthesis will fit onto a femur head where the anterior and posterior femoral cuts are angled in a wide V-shape. To achieve this, the planes of the blade guide of the anterior 49 femoral cutting block may be aligned with the x-z plane, but set at an angle thereto around the x-axis.

In one embodiment of the invention, the plane of blade guide 47 of the anterior femoral cutting block 49 is aligned with the x-z plane, and set at an angle of −10, −9, −8, −7, −6, −5, −4, −3, −2, −1, 0, 1, 2, 3, 4, 5, 6, 7, 8, 9, 10 deg around the x-axis.

To assist the surgeon, the rod guide 35 may be provided with graduations 49 against which the distance move anterior femoral cutting block 46 can be measured. The anterior femoral cutting block may by provided with one or more distance readers 92, 93. So the cut corresponds with the posterior cut, a set of graduations 59, may also be provided on the alignment device 26 to indicate the level of the posterior femoral cutting block 29. By reading the graduations 59, 59' present on the alignment device 26, the height of the anterior femoral cutting block 46 can be accurately set.

Distal Femoral Cutting Block

Figure 16A:
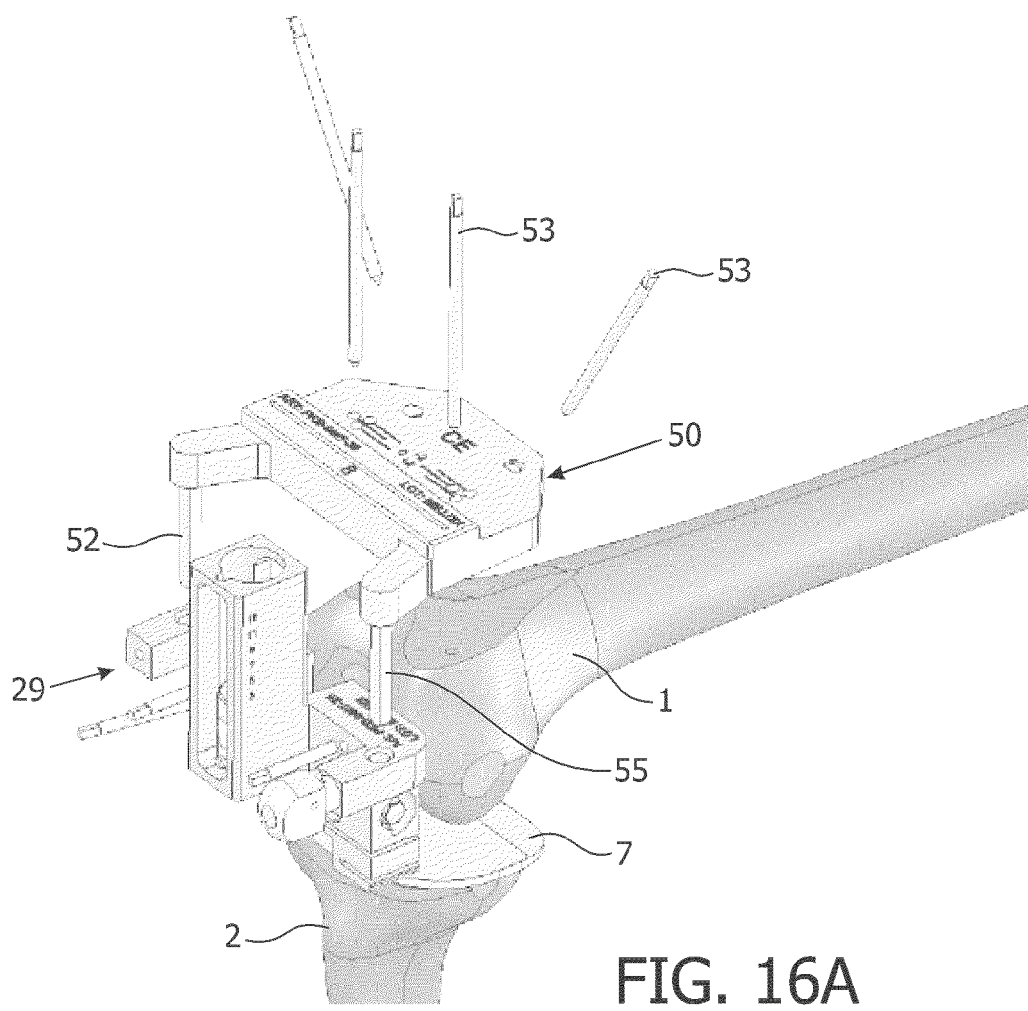
FIG. 16A shows a three dimensional view of a distal femoral cutting block prior to mounting on a posterior femoral cutting block.

The following description is made with reference to FIGS. 16A to 16 C and 17. During prosthetic knee surgery, a cut to the bone is made perpendicular to the posterior femoral cut i.e. a distal femoral cut is made. Accordingly, the present invention provides a distal femoral cutting block 50 disposed with a blade guide 51, said block provided with an attachment means 52, 55 for joining the block to the posterior femoral cutting block 29, which means 52, 55 is configured to align the plane of the blade guide 51 with the x-y plane.

According to a preferred embodiment of the invention, the distal femoral cutting block 50 comprises two or more attachment means 55, 52 which locate in two or more complementary holes 56, 57 present on the posterior femoral cutting block 29. Preferably there are two attachment means 55, 52, configured to couple with a reciprocating pair of holes located either side of the rod guide 35. Preferably an attachment means is a cylindrical rod.

The attachment means 52, 55 fixes the position and orientation of the distal cutting block 50 relative to the posterior femoral cutting block 29. Consequently, the blade guide 51 is non-adjustable. The distance of the distal cut, therefore, is selected by providing a range of distal cutting blocks 50 where the blade guide 51 is set at a different distance, which distance can be marked on the distal cutting block 50. The surgeon may select the appropriate distal cutting block according to the distances required. Readings 59 from the alignment device 26, and from the readings 49 used to position the anterior femoral cutting block 46 can be used to find the required distance. Fine tuning to the distance may be achieved by providing the posterior femoral cutting block 29 with additional holes which, depending which are used, move the distal cutting block 50 closer or further from the distal end of the femur 1. The fine adjustment provided by the choice holes can be marked 60 on the distal cutting block 50 for reference by the surgeon.

Figure 16B:
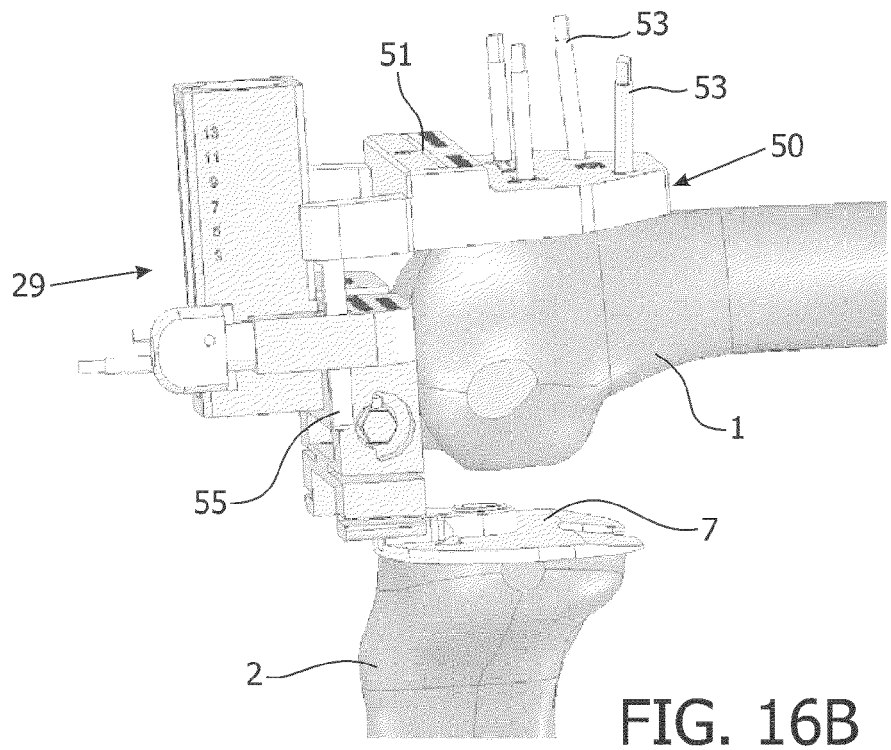
FIG. 16B shows a three dimensional view of a distal femoral cutting block attached to a posterior femoral cutting block.
Figure 16C:
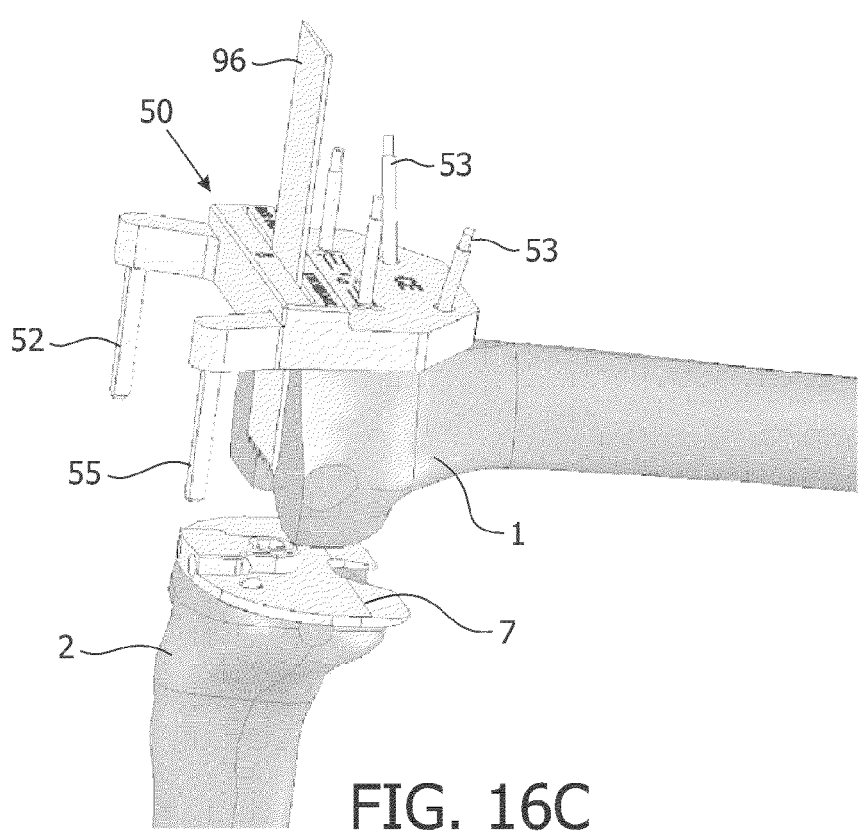
FIG. 16C shows a three dimensional view of a distal femoral cutting block attached to the femur during cutting.

FIG. 16A depicts a distal cutting block 50 prior to attachment to the posterior femoral cutting block 29. Two attachment means 55, 52, configured to couple with a reciprocating pair of holes located either side of the rod guide on the posterior femoral cutting block 29. FIG. 16B depicts a distal cutting block 50 after attachment to the posterior femoral cutting block 29; the distal cutting block 50 is held in place using pins 53 driven into the femor. FIG. 16C depicts a distal cutting blocks 50 dismounted from the posterior femoral cutting block 29 and held in place using said pins 53. The condyles are sectioned in this arrangement, using a cutting blade 96 guided through the blade guide 51.

The plane of blade guide 51 of the distal femoral cutting block 50 may or may not be exactly perpendicular with the blade guides 31, 32 of the posterior femoral cutting block 29. The blade guide of the distal femoral cutting block 50 may be aligned with the x-y plane, but set at an angle thereto around the x-axis.

In one embodiment of the invention, the plane of blade guide 51 of the distal femoral cutting block 50 is aligned with the x-y plane, and set at an angle of −10, −9, −8, −7, −6, −5, −4, −3, −2, −1, 0, 1, 2, 3, 4, 5, 6, 7, 8, 9, 10 deg around the x-axis.

Kit

The present invention may includes a kit comprising one or more of the aforementioned parts.

One embodiment of the present invention is a kit comprising one or more of the following components:
- at least one (e.g. 1, 2, 3, 4 or 5) spacing means such as for example, the above described pin 17 and keeper 85 assembly,
- a tibial plate 7 provided with a receiving slot,
- an alignment device 26,
- a posterior femoral cutting block 29,
- an anterior femoral cutting block 46,
- a distal femoral cutting block 50, It may also comprise a femoral chamfered cutting block, such block being well known in the art.

It may also comprise instructions for use. The kit may also be provided with one or more knee prosthesis.

The kit may provide components specific to a particular size of femur and prostheses. Alternatively, it may provide a range of different sizes, to accommodate different bone and prostheses sizes. For example the kit may provide a range of a distal femoral cutting blocks 50 or a range of differently sized prostheses.

The material used to manufacture the above described device maybe any suitable material that is compatible for use in surgical instruments. Examples include surgical stainless steel, titanium, carbon fibre, nickel alloys, plastics, polymers etc.

Method for Performing Knee Prosthesis Surgery

The present invention also encompasses a method for performing prosthetic knee surgery, which method is based around tensioning the knee joint while in flexion, without moving the patella to one side. The inventors have found that by pre-tensioning the joint in this way, the femoral bone cuts made after the patella is moved to one side are so accurate that the soft tissue balancing is avoided altogether or reduced.

One embodiment of the present invention is a method for performing replacement prosthetic knee surgery, after fitting a tibial plate 7, comprising the steps:
- tensioning the knee joint while in flexion, and while the patella is in place to obtain or reproduce the correct flexion gap,
- maintaining the tension using an adjustable spacing means between the fitted tibial plate 7 and the femur, and
- performing femoral bone cuts after the patella is moved to one side. The method is suitable for performing after the tibial plate 7 has been fitted.

Preferably, the spacing means enters the femur 1 through the anterior region 61 of the femoral condyle and exits though the posterior end 62 of the condyle. The spacing means applies or maintains pressure between the fitted tibial plate 7 and the femur, so the flexion gap 4 is set to the appropriate level.

Thus, another embodiment of the invention is a method as described herein, further comprising the steps of:
- making a hole (10, 11) in each femoral condyle, which hole passes through the anterior region (14) of the femoral condyle and exits though the posterior end (15),
- inserting said spacing means through said holes (10, 11), to introduce said spacing means into the flexion gap while the patella is in place.

In one embodiment of the invention, the flexion gap is adjusted by means of an inflatable balloon disposed with an inflation tube. The balloon may be inflation by air or fluid passing through the inflation tube. The uninflated balloon is inserted into in the space between the femoral condyles 5, 6 and tibial plate 7. It is generally not inserted through the hole 10, 11 that passes from the anterior 14 end of a femoral condyle 5, 6 through to the posterior 15 end of said condyle 5, 6. Instead, it may be inserted into the gap through a natural distal opening. By inflating the balloon, tension can be applied between the femoral condyles 5, 6 and tibial plate 7. Once the correct gap is achieved, the gap is maintained by the aforementioned spacing means.

The balloon and inflation tubing can be made from any suitable material such as found in a balloon catheter, for example. The balloon may be made from latex and the tubing may be made from polypropylene. The skilled person can readily prepare such an inflatable balloon based on a balloon catheter design from methods known in the art.

The knee is in flexion while the gap is maintained and the alignment device applied. The angle of flexion may be 70, 71, 72, 73, 74, 75, 76, 77, 78, 79 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 deg, or an angle in the range between any two of the aforementioned values. It is preferably 90 deg.

Figure 18:
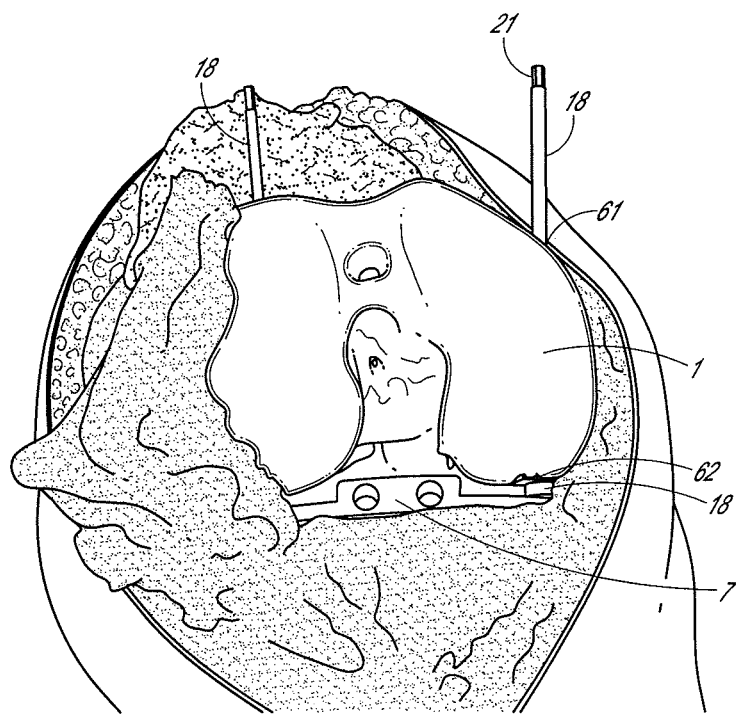
FIG. 18 shows a photograph of the spacer pins and keeper, tibial plate during surgery.

FIG. 18 depicts a view of a knee after the joint has been tensioned according to the present method; the patella has been moved aside. The spacing means comprises a set of pins 18 as already described above. Each pin enters the femur 1 through the anterior region 61 of the femoral condyle. Each pin 18 exits though the posterior end 62 of the condyle and is threaded in this part, which thread is engaged by a keeper 85. The surgeon will have adjusted the spacing means by turning the pin 18 via an hexagonal coupling 21 until the pin contacts the fitted tibial plate 7, and adjusts the flexion gap 4 to the appropriate degree.

With reference to FIG. 19, another embodiment of the present invention is the method as described above, further comprising the step of attaching the posterior femoral cutting block 29 to the tibial plate 7 using an alignment means which permits movements by the posterior femoral cutting block 29 along a y-axis, along an x-axis, and rotation about the x- and y-axes relative to a static tibial plate, where the y-axis is parallel to the intermedular tibial axis, and the x-axis is perpendicular to the plane of the y- and z-axes, where the z-axis is parallel to the intermedular femoral axis. Such alignment means may be an alignment device 26 as described above. Of course, prior to attachment, the patella is moved aside.

Figure 20:
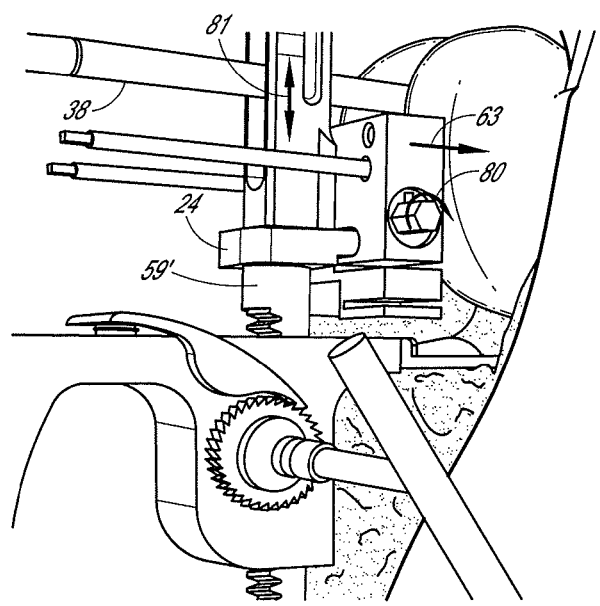
FIG. 20 shows a photograph of an alternative view from that shown in FIG. 19.

FIG. 19 shows a photograph of a knee after the step of attaching the posterior femoral cutting block 29 to the tibial plate 7, using the means described above, which is an alignment device 26. The alignment device 26 permits the movement of the cutting block 29 in the along a y-axis, which movement is indicated by arrow 81, and around an x-axis, which movement is indicated in one direction by arrow 80, and around a y-axis which movement is indicated in one direction by arrow 76. The alignment device 26 also permits movement by the block 29 along an x-axis, which movement is indicated in one direction by arrow 63 in FIG. 20. Note the movement along the x-axis allows the cutting block to mount an IM rod, regardless of the placement of the coupling means 24. Once the IM rod 38 has been mounted, movement along the x-axis (direction 63, FIG. 20) becomes restricted. The movements permitted by the alignment device allow the surgeon accurately to cut the posterior femoral condyles, and measure the depth of the cut.

Figure 21:
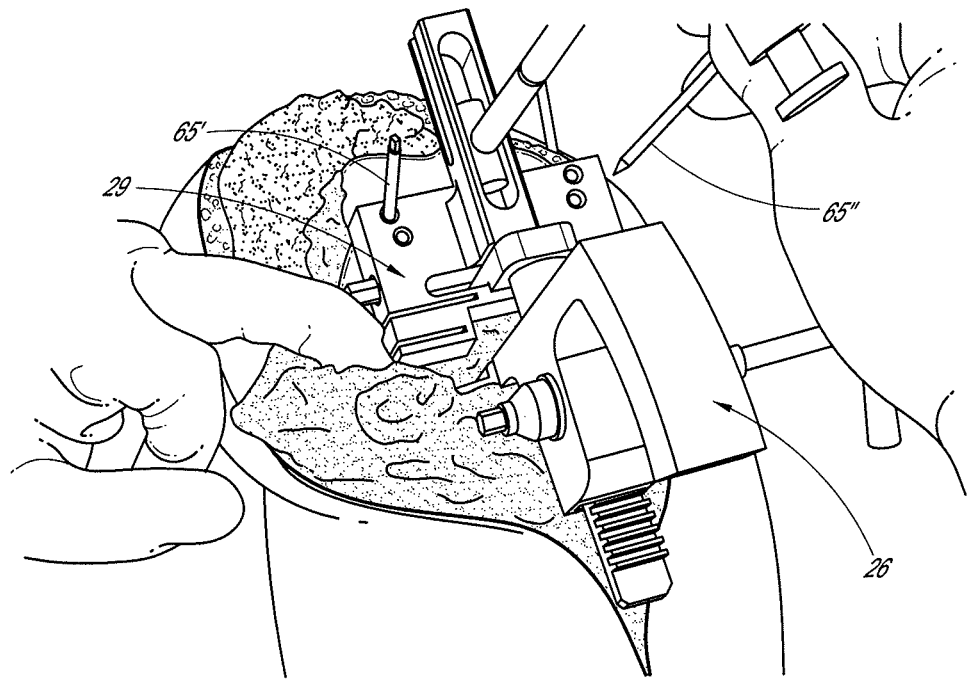
FIG. 21 shows a photograph of the surgeon inserting securing pins in to the posterior femoral cutting block.
Figure 22:
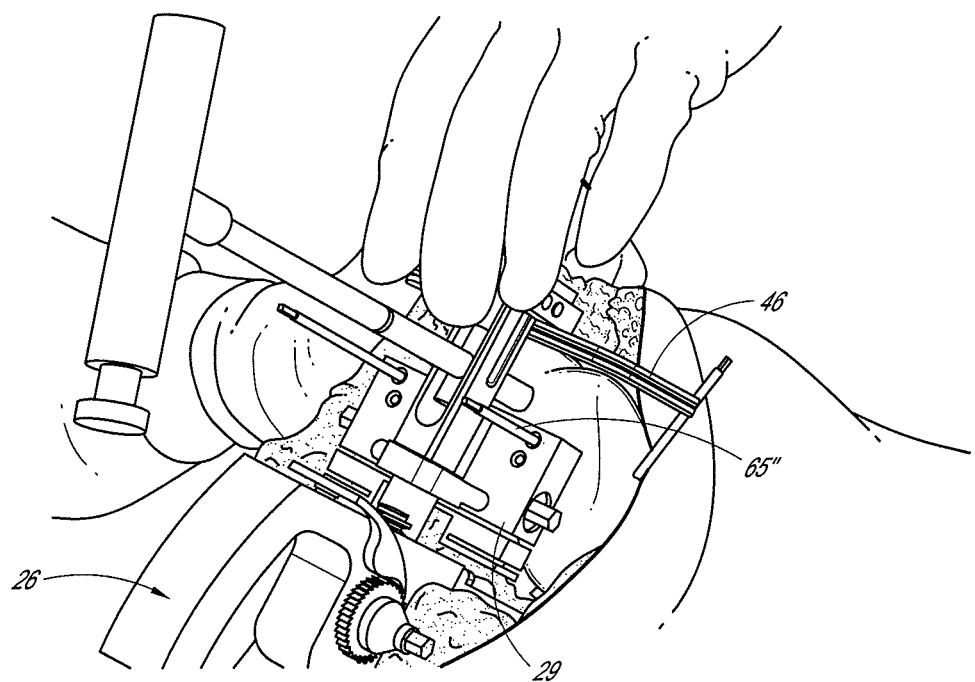
FIG. 22 shows a photograph of the surgeon aligning the anterior femoral cutting block.

With reference to FIG. 21, another embodiment of the present invention is the method as described above, further comprising the step of securing the posterior femoral cutting block 29 to the femur in the aligned position using pins 65', 65" inserted into the posterior femoral cutting block 29 and driven into the femur. Once secured, the anterior femoral cutting block 46 can be attached as described below, and then the alignment means 26 removed.

With reference to FIGS. 14A to 14D, and 22, another embodiment of the present invention is a method as described above, further comprising the step of attaching an anterior femoral cutting block 46 disposed with a blade guide 47 to the posterior femoral cutting block 29, using a means which aligns the blade guide 47 parallel with the blade guides 32 of the posterior femoral cutting block 29, and allows translational movement of the anterior femoral cutting block 46 along the rod guide 35, along an axis parallel to the y-axis. Such means 48', 48" can be a pair of rods as described above.

The surgeon may reference the height of the anterior femoral cutting block 46 according to the height of the posterior femoral cutting block 29. He may find the correct cutting height, by using graduations 49 on the rod guide 35 against which the distance moved by the anterior femoral cutting block 46 can be measured. By reading the graduations 59 present on the alignment device 26, the height of the anterior femoral cutting block 46 can be accurately set.

With the removal of the alignment means (FIG. 14A to D cf FIG. 22), the surgeon's view and freedom of movement is unobstructed, so enabling efficient resectioning using the mounted posterior femoral cutting block 29 and anterior femoral cutting block 46.

With reference to FIG. 16A to 16C, another embodiment of the present invention is a method as described above, further comprising the step of attaching a distal femoral cutting block 50 disposed with a blade guide 51 to the posterior femoral cutting block 29, using a means which aligns the blade guide 47 with the x-y plane as mentioned above, and fixes the position and orientation of the distal cutting block 50 relative to the posterior femoral cutting block 29. The anterior femoral cutting block 46 may be present or may be removed prior to attachment.

The distance of the distal cut can be selected as described above, from a range of distal cutting blocks 50 where the blade guide 51 is set at different distances. The surgeon may select the appropriate distal cutting block according to the distances 59 read from the alignment device 26, and from the distances 49 used to position the anterior femoral cutting block 46. The surgeon may also optionally choose the angle of the plane of the blade guide. After alignment, the distal cutting block 50 can be attached to the femur using pins 53 inserted through holes in the in said block and driven into the femur (FIG. 16B). After securement, of the distal cutting block 50, the posterior femoral cutting block 29. With the removal of the posterior femoral cutting block 29 (FIG. 16C), the surgeon's view and freedom of movement is unobstructed, so enabling efficient resectioning using the secured distal cutting block 50.

Once the posterior, anterior and distal femoral condyles have been cut, femur is left with three flat faces, giving an essentially square-headed profile for receiving the prosthesis. The head may be made polygonal (e.g. with five faces) by removing two of the corners. This can be achieved with the use of a femoral chamfered cutting block which fits over the anterior, posterior and distal edges of the square-headed femur, and is provided with blade guides at the appropriate angles (e.g. at 45 deg to each square face). Such cutting blocks and procedures are generally known.

The presently described method may include several intervening steps which would be known to the person skilled in the art.

What is claimed is:

1. A method for performing replacement prosthetic knee surgery, after fitting a tibial plate comprising the steps:
    making a hole in each femoral condyle, which hole passes through an anterior region of the femoral condyle and exits though a posterior end,
    inserting through each of said holes an adjustable spacing means to adjust the space between the fitted tibial plate and the femur while the knee is in flexion and a patella of the knee is in place,
    tensioning the knee joint while in flexion, while the patella is in place to obtain or reproduce a correct flexion gap,
    using the adjustable spacing means, and
    performing femoral bone cuts after the patella is moved to one side.

2. The method according to claim 1 wherein said spacing means is a device comprising at least one elongate member of dimensions for introduction through the hole that passes from the anterior end of a femoral condyle through to the posterior end of said condyle, which member is provided with an adjustable protrusion configured to protrude from the posterior end of said condyle by an amount at least equal to the flexion gap.

3. The method according to claim 2 wherein:
    said elongate member is a pin,
    said adjustable protrusion is a threaded region at least at one end of said pin, and the device further comprises a keeper provided with a threaded hole for engagement with the thread of said pin, said keeper configured to abut with the posterior end of said condyle.

4. The method according to claim 2 wherein:
    said elongate member is a pin,
    said adjustable protrusion is region provided with a plurality of inclined barbs, located at least at one end of the pin, which barbs are configured to fold back upon on contact with an entry side of the hole, and open and abut against the posterior end of said condyle at an exit side of the hole.

5. The method according to claim 2 wherein the number of elongate members is two.

6. The method according to claim 1 further comprising the step of attaching a posterior femoral cutting block to the tibial plate using an alignment means which permits movements by the posterior femoral cutting block along a y-axis and along an x-axis, and permits rotation about the x- and y-axes relative to the tibial plate, where the y-axis is parallel to the intermedular tibial axis, and the x-axis is perpendicular to the plane of the y-axis and a z-axis, where the z-axis is parallel to the intermedular femoral axis, wherein the step of attaching the posterior cutting block to the tibial plate is applied after the patella is moved to one side.

7. The method according to claim 6 wherein said alignment means is an alignment device which comprises:
    (i) a securing means for temporary attachment to the fitted tibial plate, which securing means fixes the position and orientation of the alignment device relative to the tibial plate,
    (ii) a coupling means for temporary attachment to the posterior femoral cutting block, which coupling means prevents rotation of the posterior femoral cutting block, around the z-axis, where the z-axis is parallel to the intermedular femoral axis, and
    (iii) an extending means joining (i) and (ii), which extending means is configured to adjust a distance between (i) and (ii) along the y-axis.

8. The method according to claim 7 wherein the securing means comprises a pair of pins configured for insertion into a corresponding pair of holes present on the edge of the tibial plate.

9. The method according to claim 7 wherein said coupling means permits displacement of the posterior femoral cutting block parallel to the x-axis.

10. The method according to claim 7, wherein said coupling means is a finger-like protrusion having an upper surface disposed with a flat groove, which groove is configured to engage with a pointed ridge of a receiving elongate slot present in said posterior femoral cutting block.

11. The method according to claim 7, wherein said extending means is connected to the coupling means by way of a cylindrical coupling that permits rotation of the posterior femoral cutting block around the y-axis.

12. The method according to claim 7, wherein the extending means comprises a rack-and-pinion assembly where the rack element carries the coupling means, while the pinion carries the securing means, or vice versa.

13. The method according to claim 6, further comprising the step of securing the posterior femoral cutting block to the femur in an aligned position using pins inserted into the posterior femoral cutting block and driven into the femur.

14. The method according to claim 13 wherein said posterior femoral cutting block comprises one or more blade guides, further comprising a receiving slot configured to receive a coupling means attached to an alignment device, wherein the alignment device comprises:
  (i) a securing means for temporary attachment to the fitted tibial plate, which securing means fixes the position and orientation of the alignment device relative to the tibial plate,
  (ii) a coupling means for temporary attachment to the posterior femoral cutting block, which coupling means prevents rotation of the posterior femoral cutting block, around the z-axis, where the z-axis is parallel to the intermedular femoral axis, and
  (iii) an extending means joining (i) and (ii), which extending means is configured to adjust distance between (i) and (ii) along the y-axis.

15. The method according to claim 14 wherein a plane of the blade guide is aligned with the x-z plane, and set at an angle of between −10 and +10 degrees around the x-axis.

16. The method according to claim 14, wherein the receiving slot runs parallel to the blade guides, and connects the front of the block to the back.

17. The method according to claim 14, wherein said receiving slot is wider than the coupling means, allowing the posterior femoral cutting block to move parallel to the x-axis relative to the coupling means where the x-axis is perpendicular to the y-z plane.

18. The method according to claim 14, wherein the posterior femoral cutting block further comprises an intramedular fermoral rod guide, which rod guide comprises an elongate slot oriented perpendicular to said receiving slot, and is configured to receive an intramedular femoral rod, IM rod.

19. The method according to claim 18, wherein the rod guide is configured to receive a sliding bushing, which bushing is provided with a hole through which the IM rod passes.

20. The method according to claim 19, further comprising the bushing as defined in claim 19.

21. The method according to claim 19, wherein the central axis of said hole crosses a transverse axis of the bushing by angle between −15 and 15 degrees.

22. The method according to claim 18, wherein said rod guide is an elongate structure perpendicular to the width of the receiving slot and disposed with one or more outer grooves running in an axis parallel to the y-axis, said grooves configured to receive an attachment means of the posterior femoral cutting block.

23. The method according to claim 13, further comprising the step of attaching an anterior femoral cutting block disposed with a blade guide to the posterior femoral cutting block, using a means which aligns the blade guide with the x-y plane, and allows translational movement of the anterior femoral cutting block, along an axis parallel to the y-axis.

24. The method according to claim 23 wherein said anterior femoral cutting block is provided with an attachment means for attaching to the posterior femoral cutting block, which means is configured to align a plane of the blade guide with the x-z plane.

25. The method according to claim 24 wherein said plane is set at an angle between −10 and +10 degrees around the x-axis.

26. The method according to claim 23, further comprising the steps of cutting the posterior and anterior femoral condyles using the aligned posterior femoral cutting block and anterior femoral cutting block.

27. The method according to claim 26, further comprising the step of attaching a distal femoral cutting block disposed with a blade guide to the posterior femoral cutting block, using a means which aligns the blade guide of the distal femoral cutting block with the x-y plane, and fixes the position and orientation of the distal femoral cutting block relative to the posterior femoral cutting block.

28. The method according to claim 27, wherein said distal femoral cutting block is provided with an attachment means for joining the distal femoral cutting block to the posterior femoral cutting block, which means is configured to align a plane of the blade guide of the distal femoral cutting block with an x-y plane.

29. The method according to claim 27, further comprising the step of cutting the distal femoral condyles using the aligned distal femoral cutting block.

30. The method according to claim 29, further comprising the step of removing two corners created by the aforementioned cuts to provide a chamfered femoral head for receiving the prosthesis.

31. The method according to claim 30, further comprising the step of applying the prosthesis to the chamfered femoral head.

32. The method according to claim 27, wherein the posterior femoral cutting block comprises two or more holes, the central axis of which lie in an axis parallel to the y-axis, configured to receive two or more attachment means of an anterior femoral cutting block and distal femoral cutting block, such that a plane of the blade guide of the anterior femoral cutting block aligns with the x-z plane and a plane of the blade guide of the distal femoral cutting block aligns with the x-y plane.

33. A method for performing replacement prosthetic knee surgery, after fitting a tibial plate comprising the steps:
  tensioning the knee joint while in flexion, while a patella of the knee is in place to obtain or reproduce a correct flexion gap,
  maintaining the tension using an adjustable spacing means between the fitted tibial plate and the femur, and performing femoral bone cuts after the patella is moved to one side,
  wherein said spacing means is a device comprising at least one elongate member of dimensions for introduction through a hole that passes from an anterior end of the femoral condyle through to the posterior end of said condyle, which member is provided with an adjustable protrusion configured to protrude from the posterior end of said condyle by an amount at least equal to the flexion gap.

* * * * *